(12) United States Patent
Surridge et al.

(10) Patent No.: US 8,506,775 B2
(45) Date of Patent: Aug. 13, 2013

(54) DEVICES AND METHODS RELATING TO ELECTROCHEMICAL BIOSENSORS

(75) Inventors: Nigel Anthony Surridge, Carmel, IN (US); Paul Douglas Walling, Indianapolis, IN (US); Melani Sullivan, Minneapolis, MN (US); Vladimir Svetnik, Morristown, NJ (US); Brian S. Hill, Avon, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1848 days.

(21) Appl. No.: 10/872,008

(22) Filed: Jun. 18, 2004

(65) Prior Publication Data

US 2005/0023152 A1    Feb. 3, 2005

Related U.S. Application Data

(60) Provisional application No. 60/480,243, filed on Jun. 20, 2003.

(51) Int. Cl.
*C12M 1/00* (2006.01)

(52) U.S. Cl.
USPC ........................................ 204/403.1

(58) Field of Classification Search
USPC ..................... 205/775; 204/403.1
See application file for complete search history.

(56) References Cited

U.S. PATENT DOCUMENTS

| | | | |
|---|---|---|---|
| 5,120,420 A | 6/1992 | Nankai et al. | |
| 5,384,028 A | 1/1995 | Ito | |
| 5,677,546 A | 10/1997 | Yu | |
| 5,698,083 A * | 12/1997 | Glass | 204/403.03 |

(Continued)

FOREIGN PATENT DOCUMENTS

| | | |
|---|---|---|
| EP | 1 253 204 A2 | 10/2002 |
| EP | 1 281 955 A1 | 2/2003 |

(Continued)

OTHER PUBLICATIONS

Niwa, Osamu et al.; Electrochemical Behavior of Reversible Redox Species at Interdigitated Array Electrodes with Different Geometries: Consideration of Redox Cycling and Collection Efficiency; Anal. Chem.; 1990; 447-452; 62; Ibaraki, Japan.

Tanaka, Mitsuya et al.; Voltammetry at Geometrically Uneven Electrodes: Part 1, Chronoamperometry at Model Electrodes with Rectangular Hollow or Protrusive Surfaces; J. Electroanal. Chem.; 1988; 1-14; 246; The Netherlands.

(Continued)

*Primary Examiner* — Jennifer Michener
*Assistant Examiner* — Dustin Q Dam
(74) *Attorney, Agent, or Firm* — Woodard, Emhardt, Moriarty, McNett & Henry LLP

(57) ABSTRACT

A system for testing for analytes in a sample of biological fluid includes a test strip that defines a cavity for receiving the sample. At least two sets of electrodes are adjacent the sample cavity, including one for measuring one property of the sample, and another for measuring one or more other properties of the sample, such as temperature and/or the presence or magnitude of confounding variables. The measurements are combined to yield the desired result. At least one set of working and counter electrodes each have a plurality of elongated "fingers" interdigitated with those of the other electrode in the set. The gaps between fingers can be quite small, so that the two electrode sets together can operate in a small measurement volume of sample. Additional electrodes can be included that measure the presence or sufficiency of the sample, and additional traces on the strip can act as configuration identifiers.

59 Claims, 15 Drawing Sheets

(56) References Cited

U.S. PATENT DOCUMENTS

| | | | |
|---|---|---|---|
| 5,766,789 | A | 6/1998 | James et al. |
| 5,830,341 | A * | 11/1998 | Gilmartin ............... 205/777.5 |
| 5,897,522 | A | 4/1999 | Nitzan |
| 5,985,116 | A | 11/1999 | Ikeda et al. |
| 6,036,924 | A | 3/2000 | Simmons et al. |
| 6,287,451 | B1 * | 9/2001 | Winarta et al. ........... 205/777.5 |
| 6,319,719 | B1 | 11/2001 | Bhullar et al. |
| 6,540,890 | B1 | 4/2003 | Bhullar et al. |
| 6,612,111 | B1 | 9/2003 | Hodges et al. |
| 6,743,635 | B2 | 6/2004 | Neel et al. |
| 6,814,844 | B2 | 11/2004 | Bhullar et al. |
| 7,022,218 | B2 * | 4/2006 | Taniike et al. ............ 205/777.5 |
| 7,041,206 | B2 | 5/2006 | Gephart et al. |
| 7,244,264 | B2 | 7/2007 | Roe et al. |
| 7,501,053 | B2 * | 3/2009 | Karinka et al. ............ 205/792 |
| 7,625,457 | B2 | 12/2009 | Roe et al. |
| 7,727,467 | B2 | 6/2010 | Burke et al. |
| 7,829,023 | B2 | 11/2010 | Burke et al. |
| 2002/0090649 | A1 * | 7/2002 | Chan et al. ............... 435/7.1 |
| 2002/0170823 | A1 | 11/2002 | Housefield et al. |
| 2002/0192115 | A1 | 12/2002 | Bhullar et al. |
| 2003/0004403 | A1 | 1/2003 | Drinan et al. |
| 2003/0046811 | A1 | 3/2003 | Chang et al. |
| 2003/0146436 | A1 | 8/2003 | Parker et al. |
| 2003/0155237 | A1 | 8/2003 | Surridge et al. |
| 2003/0175946 | A1 | 9/2003 | Tokunga et al. |
| 2003/0185705 | A1 | 10/2003 | Otake |
| 2003/0214304 | A1 * | 11/2003 | Karinka et al. ............ 324/444 |
| 2004/0186394 | A1 | 9/2004 | Roe et al. |
| 2004/0251131 | A1 | 12/2004 | Ueno et al. |
| 2004/0256248 | A1 | 12/2004 | Burke et al. |
| 2006/0057707 | A1 | 3/2006 | Cunningham et al. |
| 2008/0314882 | A1 | 12/2008 | Bhullar et al. |

FOREIGN PATENT DOCUMENTS

| | | |
|---|---|---|
| JP | 2002-535615 A | 10/2002 |
| JP | 2003-014687 A | 1/2003 |
| JP | 2003-511851 | 3/2003 |
| JP | 2003-149192 A | 5/2003 |
| WO | WO 99/29429 | 6/1999 |
| WO | WO 00/19185 | 4/2000 |
| WO | WO 00/33063 | 6/2000 |
| WO | WO 00/42422 A1 | 7/2000 |
| WO | WO 01/25775 A1 | 4/2001 |
| WO | WO 02/054055 | 7/2002 |
| WO | WO 02/086483 A1 | 10/2002 |
| WO | WO 03/056345 A1 | 7/2003 |
| WO | WO 2004/034053 A2 | 4/2004 |
| WO | WO 2005/124331 | 12/2005 |

OTHER PUBLICATIONS

Aoki, Koichi and Tanaka, Mitsuya; Time-Dependence of Diffusion-Controlled Currents of a Soluble Redox Couple at Interdigitated Microarray Electrodes; J. Electroanal. Chem.; 1989; 11-20; 266; The Netherlands.

Aoki, Koichi; Theory of the Steady-State Current of a Redox Couple at Interdigitated Array Electrodes of Which Pairs are Insulated Electrically by Steps; J. Electroanal. Chem.; 1989; 35-41; 270; The Netherlands.

Aoki, Koichi; Approximate Models of Interdigitated Array Electrodes for Evaluating Steady-State Currents; J. Electroanal. Chem.; 1990; 35-42; 284; The Netherlands.

Aoki, Koichi et al.; Theory of Charge Transport Within Polymer Films With Uneven Thickness Coated on Electrodes; J. Electroanal. Chem.; 1984; 139-150; 176; The Netherlands.

Aoki, Koichi et al.; Reversible Square-Wave Voltammograms: Independence of Electrode Geometry; J. Electroanal. Chem.; 1986; 25-39; 207; The Netherlands.

Matsuda, Hiroaki et al.; Theory of Electrode Reactions of Redox Couples Confined to Electrode Surfaces at Monolayer Levels; Part I. Expression of the Current-Potential Relationship for Simple Redox Reactions; J. Electroanal. Chem.; 1987; 1-13; 217; The Netherlands.

Matsuda, Hiroaki et al.; Theory of Electrode Reactions of Redox Couples Confined to Electrode Surfaces at Monolayer Levels; Part II. Cyclic Voltammetry and AC Impedance Measurements: J. Electroanal. Chem.; 1987; 15-32; 217; The Netherlands.

Aoki, Koichi et al.; Theory of Chromoamperometric Curves at Microband Electrodes; J. Electroanal. Chem.; 1987; 19-32; 225; The Netherlands.

Aoki, Koichi et al.; Derivation of an Approximate Equation for Chronoamperometric Curves at Microband Electrodes and its Experimental Verification; J. Electroanal. Chem.; 1987; 61-67; 230; The Netherlands.

Aoki, Koichi et al.; Quantitative Analysis of Reversible Diffusion-Controlled Currents of Redox Soluble Species at Interdigitated Array Electrodes Under Steady-state Conditions; J. Electroanal. Chem.; 1988; 269-282; 256; The Netherlands.

Aoki, Koichi et al.; Derivation of an Approximate Equation for Chronoamperometric Curves at Microbank Electrodes and Its Experimental Verification; J. Electroanal. Chem.; 1987; 61-67; 230; The Netherlands.

Aoki, Koichi et al.; Theory of Chronoamperometric Curves at Microband Electrodes; J. Electroanal. Chem.; 1987; 19-32; 225; The Netherlands.

Chidsey, Christopher E. et al.; Micrometer-Spaced Platinum Interdigitated Array Electrode: Fabrication, Theory, and Initial Use; Anal. Chem.; 1986; 601-607; 58; Murray Hill, NJ, US.

Feldman, B.J. et al.; Electron Transfer Kinetics at Redox Polymer/Solution Interfaces Using Microelectrodes and Twin Electrode Thin Layer Cells; J. Electroanal. Chem.; 1985; 63-81; 194; The Netherlands.

Feldman, B.J. and Murray, Royce W.; Electron Diffusion in Wet and Dry Prussian Blue Films on Interdigitated Array Electrodes; Amer. Chem. Soc.; 1987; 1702-1708; 26; Chapel Hill, NC, US.

Feldman, B.J. and Murray, Royce W.; Measurement of Electron Diffusion Coefficients Through Prussian Blue Electroactive Films Electrodeposited on Interdigitated Array Platinum Electrodes; Amer. Chem. Soc.; 1986; 2844-2847; 58; Chapel Hill, NC, US.

Anderson, Larry B. and Reilley, Charles N.; Thin-Layer Electrochemistry: Steady-State Methods of Studying Rate Processes; J. Electroanal. Chem.; 1965; 295-305; 10; Chapel Hill, NC, US.

Kirowa-Eisener, H. Reller E. and Gileadi, E.; Ensembles of Microelectrodes: A Digital Simulation; J. Electroanal. Chem.; 1982; 65-77; 138; The Netherlands.

Anderson, James L. et al.; Hydrodynamic Voltammetry at an Interdigitated Electrode Array in a Flow Channel: *Part I. Numerical Simulation*; J. Electroanal. Chem.; 1985; 213-226; 196; The Netherlands.

Aoki, Koichi and Osteryoung, Janet; Diffusion Controlled Current at a Stationary Finite Disk Electrode: Experiment; J. Electoanal. Chem.; 1981; 315-320; 125; The Netherlands.

Aoki, Hoichi et al.; Quantitative Analysis of Reversible Diffusion-Controlled Currents of Redox Soluble Species at Interdigitated Array Electrodes Under Steady-State Conditions; J. Electroanal. Chem.; 1988; 269-282; 256; The Netherlands.

Foster, Robert et al.; Electrochemical Diagnostic Strip Device for Total Cholesterol and Its Subfractions: Electroanalysis; 2000; 716-721; vol. 12; No. 9; Gwynedd; UK.

Niwa, Osamu et al.; Fabrication and Characteristics of Vertically Separated Interdigitated Array Electrodes; J. Electroanal. Chem.; 1989; 291-297; 267; The Netherlands.

Horluchl, Tsutomu et al.; Detection of Reversible Redox Species by Substitutional Stripping Voltammetry; Anal. Chem.; 1994; 1224-1230; 66; Ibaraki, Japan.

Canadian Patent Application No. 2,529,579 Office Action mailed Nov. 26, 2009.

Japanese Patent Application No. 517450/2006 Office Action mailed Dec. 15, 2009.

U.S. Appl. No. 10/871,843 to Bhullar et al., Notice of Allowance mailed Oct. 5, 2010.

* cited by examiner

DEVICES AND METHODS RELATING TO ELECTROCHEMICAL BIOSENSORS

REFERENCE TO RELATED APPLICATIONS

This application claims priority to U.S. Provisional Application No. 60/480,243, titled "DEVICES AND METHODS RELATING TO ELECTROCHEMICAL BIOSENSORS," This application is also related to applications titled SYSTEM AND METHOD FOR ANALYTE MEASUREMENT USING AC EXCITATION (U.S. application Ser. No. 10/688,343, "AC Excitation application" herein), METHOD OF MAKING A BIOSENSOR (case number RDID-9958-CIP-US, "Biosensor application" herein), and DEVICES AND METHODS RELATING TO ANALYTE SENSORS (U.S. Provisional Application No. 60/480,397, "Analyte Sensors application" herein), which were all filed on Jun. 20, 2003, and to U.S. patent application Ser. No. 10/264,891 (entitled "ELECTRODES, METHODS, APPARATUSES COMPRISING MICRO-ELECTRODE ARRAYS", filed Oct. 4, 2002), which are all incorporated herein by reference in their entireties.

BACKGROUND

The present invention relates to devices, systems, and methods for measuring analytes from biological samples, such as from a sample of bodily fluid. More specifically, the present invention relates to biosensors and methods for testing an analyte using certain electrical response characteristics.

Measuring the concentration of substances, particularly in the presence of other, confounding substances ("interferents"), is important in many fields, and especially in medical diagnosis and disease management. For example, the measurement of glucose in bodily fluids, such as blood, is crucial to the effective treatment of diabetes.

Multiple methods are known for measuring the concentration of analytes such as glucose in a blood sample. Such methods typically fall into one of two categories: optical methods and electrochemical methods. Optical methods generally involve absorbance, reflectance or laser spectroscopy to observe the spectrum shift in the fluid caused by the concentration of the analytes, typically in conjunction with a reagent that produces a known color when combined with the analyte. Electrochemical methods generally rely upon the correlation between a charge-transfer or charge-movement property of the blood sample (e.g., current, interfacial potential, impedance, conductance, and the like) and the concentration of the analyte, typically in conjunction with a reagent that produces or modifies charge-carriers when combined with the analyte. See, for example, U.S. Pat. No. 4,919,770 to Preidel, et al., and U.S. Pat. No. 6,054,039 to Shieh, which are incorporated by reference herein in their entireties.

An important limitation of electrochemical methods of measuring the concentration of a chemical in blood is the effect of confounding variables on the impedance of a blood sample. For example, the geometry of the blood sample must correspond closely to that upon which the impedance-to-concentration mapping function is based.

The geometry of the blood sample is typically controlled by a sample-receiving portion of the testing apparatus. In the case of blood glucose meters, for example, the blood sample is typically placed onto a disposable test strip that plugs into the meter. The test strip may have a sample chamber to define the geometry of the sample. Alternatively, the effects of sample geometry may be limited by assuring an effectively infinite sample size. For example, the electrodes used for measuring the analyte may be spaced closely enough so that a drop of blood on the test strip extends substantially beyond the electrodes in all directions. Regardless of the strategy used to control sample geometry, typically one or more dose sufficiency electrodes are used to assure that there is a sufficient amount of sample to assure an accurate test result.

Other examples of limitations to the accuracy of blood glucose measurements include variations in blood chemistry (other than the analyte of interest being measured). For example, variations in hematocrit (concentration of red blood cells) or in the concentration of other chemicals, constituents or formed elements in the blood, may affect the measurement. Variation in the temperature of blood samples is yet another example of a confounding variable in measuring blood chemistry.

Thus, a system and method are needed that accurately measure blood glucose, even in the presence of confounding variables, including variations in temperature, hematocrit, and the concentrations of other chemicals in the blood. A system and method are likewise needed that accurately measure an analyte in a fluid. It is an object of the present invention to provide such a system and method.

Many approaches have been employed to attenuate or mitigate the influence of one or more sources of interference, or to otherwise compensate for or correct a measured value. Often multiple design solutions are employed to adequately compensate for the sensitivities associated with the chosen measurement method.

Well known design solutions involve perm-selective and/or size-selective membranes, filters or coatings. Such design solutions suffer from incremental costs of goods, additive manufacturing process steps further exacerbating manufacturing cost, complexity, and speed of manufacture. Systems (disposable test strips and instruments) employing these methods take the general approach of overcoming the problem within the scope of the test strip design.

Another general approach involves the use of sophisticated excitation and signal processing methods coupled with co-optimized algorithms. Simpler, less complex, test strip architectures and manufacturing processes may be realized; however, instrumentation costs, memory and processor requirements, associated complex coding, and calibrated manufacturing techniques are required. Systems employing this technique take the general approach of overcoming the problem within the scope of the instrumentation.

A more recent approach involves neither the strip nor instrumentation, per se, but rather exploits the measurement methodology. An example of this is the use of a coulometric method to attenuate the influence of hematocrit and temperature.

It is also well known to those skilled in the art that all of the above approaches are further supported by the initial design of reagent systems. In the detection of glucose, for example, this may involve the use of selective redox mediators and enzymes to overcome the detrimental influence of redox-active species or the presence of other sugars.

It is an object of the invention to provide a simpler, less costly method for attenuating the influence of interferents, in a manner that does not suffer the demerits associated with the general approaches currently in wide use.

SUMMARY

Two Pairs Generally.

In one aspect, the present invention involves the provision of two pairs of electrodes, which allow for the use of two measurements to correct or compensate the analyte measurement for interferents. In one embodiment for example, a pair of electrodes defines a first measurement zone, while a second pair defines a second measurement zone. The pairs are roughly coplanar, and within a pair of electrodes each has a length substantially parallel to the length of the other. At least one of the electrodes in the first pair of electrodes comprises at least two elongated, rectangular conductive elements, which are interdigitated with the conductive element(s) of the other electrode in the pair. Each element for an electrode is conductively connected to the same contact for electrical communication with a driver and/or meter. The sample establishes electrical contact with both pairs after dosing.

Several variations of the foregoing are contemplated. For example, in one approach a reagent or a plurality of reagents can be selectively deployed onto at least one of the at least two pairs of electrodes residing in a sample chamber. Both pairs are coated with a first reagent. Optionally, one of the two pairs is coated with a first reagent, and the second pair is coated with the same reagent but lacking either enzyme or mediator. Alternatively, one of the two pairs is coated with a first reagent and the other pair is coated with a second reagent. In another embodiment, one of at least two pairs is coated with a reagent and the other pair lacks a reagent coating, with the downstream pair preferably having the reagent coating. In a variation of this embodiment, the other of the pairs is covered with a coating that is perm-selective, size-selective, or otherwise affects the electrode response in the presence of one or more analytes and/or interferents.

In further aspects, dose detection and dose sufficiency electrodes are included. For example, a third electrode system may be included that is located further from the edge than the first two electrode pairs, i.e. is downstream of the entering sample fluid, and is operable to detect when there is sufficient sample fluid to conduct an accurate test. This third electrode system may comprise a single electrode element or a plurality of elements. In single-element embodiments, the element functions in combination with one or more of the other electrodes to test for sample sufficiency. Alternatively, the dose sufficiency electrode system may comprise a pair of electrode elements that cooperate with one another to evidence sample sufficiency. A comparable electrode system may similarly be employed to detect when a sample fluid has been applied to the biosensor.

DESCRIPTION

Figure 1:
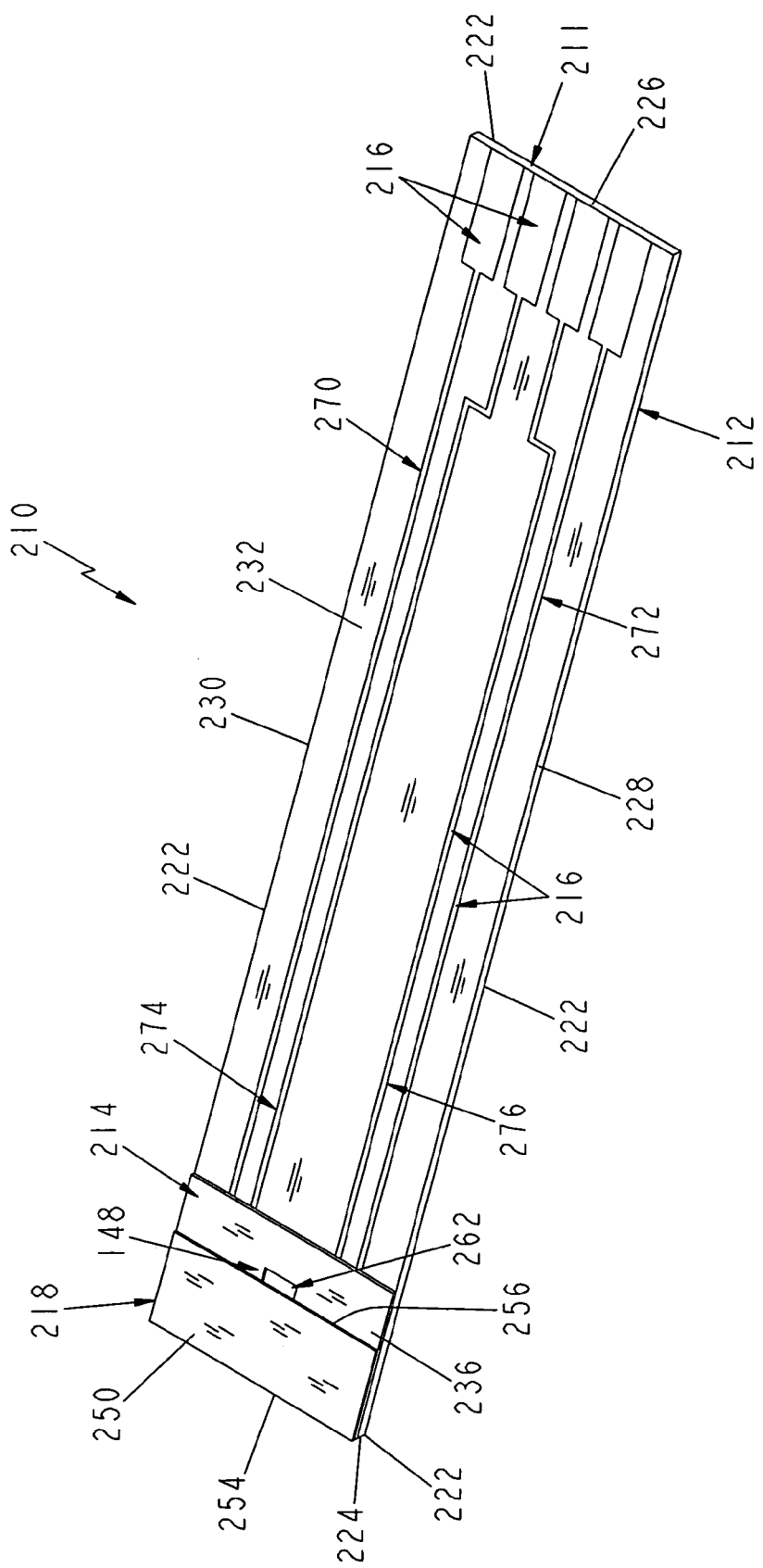
FIG. 1 is a perspective view of a testing strip according to one embodiment of the present invention.

For the purpose of promoting an understanding of the principles of the present invention, reference will now be made to the embodiments illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein are contemplated as would normally occur to one skilled in the art to which the invention relates.

Introduction

Generally, the test strips of the present invention provide for testing of an analyte in a bodily or other fluid using multiple electrode arrays that perform different functions or have different response functions with the sample. One particular embodiment involves the combination of macro-electrodes and micro-electrodes that operate in respective pairs, but contribute information for a final determination of the analyte concentration, such as by having the information obtained from one electrode pair being used to compensate or correct the results obtained from the other electrode pair, or by combining the responses of the electrode pairs in a predetermined fashion.

These electrode arrays may also be combined in a wide variety of other ways to accomplish multiple related functions, including analyte concentration, detection of hematocrit, determination of correction factors, as well as sample sufficiency and dose detection, all on a single strip and in an extremely small space. Alternatively, by using multiple arrays with different sensitivities to interferents, one may exploit the two measurements to provide a more accurate result, as would normally occur to one skilled in the art.

In various embodiments, different electrochemical excitation techniques (for example, DC, AC phase, AC amplitude, or combined DC/AC) are applied to these different electrode arrays to achieve the desired goals. Examples of such techniques are well known in the art, and are further exemplified in the AC Excitation application, which was incorporated above by reference.

Another exemplary technique compensates for variation of diffusion coefficients of the electrochemically active species being tested. Faradaic current in soluble reagents at an electrode surface occurs due to the physical diffusion of these species and the value of the diffusion coefficient influences the measured response. Commercial systems are often calibrated and built such that the nominal sensor response (faradaic current) to a given amount of glucose is repeatable if the diffusion coefficients remain fixed. Unfortunately both the temperature and hematocrit (HCT) of each individual sample alter the effective diffusion coefficient of the electroactive species being measured. If these factors are not considered, the glucose measurement can be in error for any temperature or hematocrit value differing from those used in the calibration of the system.

In this exemplary technique, the system determines the faradaic response of an electrochemical sensor due to an analyte of interest, and provides an estimate of the actual, effective diffusion coefficient of the species undergoing the redox reaction at the electrode surface. In particular, the system compensates for diffusion coefficient variation by using two electrode systems (preferably of different types) exposed to the same reagent-sample mixture. Soluble, electroactive species, such as the redox mediators commonly employed in glucose biosensors, diffuse to a planar, macro-electrode yielding a current response to a potential step according to the Cottrell equation (1).

$$i_p = nFA_p C \sqrt{\frac{D}{\pi t}} \quad \text{so that} \tag{1a}$$

$$\lim_{t \to /(\infty)} i_p = 0 \tag{1b}$$

where n is the number of electrons involved in the electron transfer, F is the Faraday constant (96,485.3 C/equivalent), $A_p$ is the area of the macro-electrodes in contact with the solution, C is the concentration of the analyte in the sample, D is the effective diffusion coefficient of the species, and $i_p$ is the current response at the macro-electrode.

It will similarly be understood by those of skill in the art that the response of these same species to the same potential step at a micro-electrode would yield a current response characterized by equation (2).

$$i_s = nFA_sC\sqrt{\frac{D}{\pi t}} + \frac{vnFA_sCD}{r_o} \quad \text{so that} \quad (2a)$$

$$\lim_{t\to(\infty)} i_s = \frac{nFA_sCD}{r_o} \quad (2b)$$

where $A_s$ is the area of the micro-electrode, v is an electrode shape-dependent accessibility factor and $i_s$ is the current response at the micro-electrode at the micro-electrode. In equations (1b) and (2b), t(∞) means a time sufficiently long that the condition of "semi-infinite" or "steady-state" diffusion, respectively, can be established at the electrodes in question.

One embodiment would apply the same potential between (a) the planar, macro electrode and a counter/reference electrode, and between (b) the micro electrode(s) and counter/reference electrode. The time-dependent current response would then be measured at several time-points following potential application at both macro and microelectrodes. An analysis of $$i_p = f\left(\frac{1}{\sqrt{t}}\right)$$

would produce $slope_p$, as in equation (3), while the same analysis of $$i_s = f\left(\frac{1}{\sqrt{t}}\right)$$

would yield an $intercept_s$ as shown in equation (4).

$$slope_p = nFA_pC\sqrt{\frac{D}{\pi}} \quad (3)$$

$$intercept_s = \frac{nFA_sCD}{r_o} \quad (4)$$

Given that in this invention both $i_p$ and $i_s$ are derived from the same reaction and sample, it is possible to calculate an apparent diffusion coefficient for the electrochemically reacting species in the device, independent of the concentration of the species according to equation (5), where the areas of the two electrode types, $A_s$ and $A_p$, as well as the radius of the micro-electrode(s), $r_o$, are known. For example, a spherical microelectrode yields:

$$\frac{intercept_s}{slope_p} = \frac{A_s\sqrt{\pi D}}{r_o A_p} \quad (5)$$

Once D is estimated, it can be applied in a number of different ways to provide a correction for the measured concentration, C, of the electrochemical species. Some embodiments simply use the estimated value of D in equation (3) to calculate C. Such a determination of C is less subject to uncompensated variation in D as is common in amperometric sensors whose current response is largely described by equation (1). It is also noteworthy that the correction is independent of the cause of variation in D (e.g., temperature, hematocrit, viscosity change, etc.)—the correction is provided by the different functional dependence of the two electrode pairs on the chemical properties of the sample.

In each of the strips illustrated herein, an electrode array is used to measure an analyte, such as glucose, in a sample. When the sample reaches the array, it combines with reagent that is placed adjacent to the array to provide certain properties of electrical impedance in the presence of a certain electrical signal, as is understood in the art, which impedance is used as a first datum. Another array, either upstream or downstream from the first array, but preferably not covered by a reagent, is used to provide another electrical stimulus to the sample, and the electrical response at the array is used as a second datum affected in a known way by an interferent, such as hematocrit temperature, or the like. This two data are combined to yield a corrected analyte concentration value. The two arrays can be used at the same time to analyze a single sample in a common volume of very small dimensions.

General Information

System

The present invention relates to a system that is useful for assessing an analyte in a sample fluid. The system includes devices and methods for evaluating the sample fluid for the target analyte. The evaluation may range from detecting the presence of the analyte to determining the concentration of the analyte. The analyte and the sample fluid may be any for which the test system is appropriate. For purposes of explanation only, a preferred embodiment is described in which the analyte is glucose and the sample fluid is blood or interstitial fluid. However, the present invention clearly is not so limited in scope.

Sensor

One component of the system is an electrochemical sensor including a sample-receiving chamber for the sample fluid, and a reagent for producing an electrochemical signal in the presence of the test analyte. The sensor preferably comprises a disposable test strip, particularly one having a laminar construction providing an edge opening to a sample-receiving chamber. The reagent is disposed within the sample-receiving chamber in position to provide the electrochemical signal to a working electrode also positioned within the chamber. In appropriate circumstances, such as for glucose detection, the reagent may contain an enzyme and optionally a mediator.

Meter

The sensor is used in combination with a meter for determination of the presence and/or concentration of the analyte in the sample fluid. The meter conventionally includes a connection with the electrodes of the sensor and circuitry to evaluate the electrochemical signal corresponding to the concentration of the analyte. The meter may also include means for determining that the sample fluid has been received by the sensor, and that the amount of sample fluid is sufficient for testing. The meter typically will store and display the results of the analysis, or may alternatively provide the data to a separate device.

Analyte—Characteristic

The system can provide either a qualitative or quantitative indication for the analyte. In one embodiment, the system indicates simply the presence of the analyte in the sample fluid. The system may also provide a reading of the quantity or concentration of the analyte in the sample fluid. In a preferred embodiment, it is a feature of the present invention that a highly accurate and precise reading of the analyte concentration is obtained.

Analyte—Type

The system is useful for the determination of a wide variety of analytes. The test strip, for example, is readily adapted for use with any suitable chemistry that can be used to assess the presence of the analyte. Most preferably, the system is configured and used for the testing of an analyte in a biological fluid. Such analytes may include, for example, glucose, lactate, urate, ketones, etc. Commensurate modifications to the system will be apparent to those skilled in the art. For purposes of explanation, and in a particularly preferred embodiment, the system is described with respect to the detection of glucose in a biological fluid.

Interferents

Test methodologies may be variously affected by the presence of interferents in the sample fluid. For example, the testing for glucose in a blood sample may be impacted by such factors as bilirubin, hematocrit, uric acid, ascorbate, acetaminophen, galactose, maltose, and lipids. The present system is adaptable to minimize or eliminate the adverse effects of interferents that may also be present in the sample fluid. These effects may be addressed by appropriate selection of test materials and parameters, such as by the selection of chemistries that are known to be impacted less, or not at all, by possible interferents. They may also be addressed by selection of two or more reagents that have differential sensitivities to the interferent, but substantially the same sensitivity to the analyte of interest. As is known in the art, other steps may also be taken to deal with possible interferent effects, such as the use of coatings or films that prevent the interferent from entering the test zone. In addition, modifications to the electrode configurations or interrogation methods can be used to minimize the effect of interferents.

Fluid Type

The system is useful with a wide variety of sample fluids, and is preferably used for the detection of analytes in a biological fluid. In this context, the term "biological fluid" includes any body fluid in which the analyte can be measured, for example, interstitial fluid, dermal fluid, sweat, tears, urine, amniotic fluid, spinal fluid and blood. The term "blood" in the context of the invention includes whole blood and its cell-free components, namely plasma and serum. In addition, the system is useful in connection with reference fluids that are used in conventional fashion to verify the integrity of the system for testing.

In a preferred embodiment, the system is employed for the testing of glucose. The sample fluid in this instance may specifically include, for example, fresh capillary blood obtained from the finger tip or approved alternate sites (e.g., forearm, palm, upper arm, calf and thigh), fresh venous blood, and control solutions supplied with or for the system.

The fluid may be acquired and delivered to the test strip in any fashion. For example, a blood sample may be obtained in conventional fashion by incising the skin, such as with a lancet, and then contacting the test strip with fluid that appears at the skin surface. It is an aspect of the present invention that the test strip is useful with very small fluid samples. It is therefore a desirable feature of the invention that only a slight incising of the skin is necessary to produce the volume of fluid required for the test, and the pain and other concerns with such method can be minimized or eliminated.

Electrodes

Electrode Type

The invention relates to an "electrochemical sensor", which is a device configured to detect the presence and/or measure the concentration of an analyte by way of electrochemical oxidation and reduction reactions within the sensor, and/or development of movement of charged layers within the solution. These reactions are transduced to an electrical signal that can be correlated to an amount or concentration of the analyte. The test strip therefore includes an electrode system comprising at least a working electrode and a counter electrode within the sample receiving chamber. The sample receiving chamber is configured such that sample fluid entering the chamber is placed in electrolytic contact with both the working electrode and the counter electrode. This allows electrical current to flow between the electrodes to effect the electrooxidation or electroreduction of the analyte or its products.

In the context of the present invention, a "working electrode" is an electrode at which analyte or product is electrooxidized or electroreduced with or without the agency of a redox mediator. The term "counter electrode" refers herein to an electrode that is paired with the working electrode and through which passes an electrochemical current equal in magnitude and opposite in sign to the current passed through the working electrode. The term "counter electrode" is meant to include counter electrodes that also function as reference electrodes (i.e., a counter/reference or auxiliary electrode).

Electrode Material

The working and counter electrodes, and the remaining portions of the electrode system, may be formed from a variety of materials, as known in the art. The electrodes should have a relatively low electrical resistance and should be electrochemically inert over the operating range of the test strip. Suitable conductors for the working electrode include gold, palladium, platinum, carbon, titanium, ruthenium dioxide, iridium, and indium tin oxide, as well as others, such as the conductors disclosed in the Analyte Sensors application, which was incorporated above by reference. The counter electrode may be made of the same or different materials. In a preferred embodiment, both of the electrodes are gold electrodes.

Electrode Application

The electrode systems utilized by the present invention may be applied to the base substrate in any fashion that yields electrodes of adequate conductivity and integrity. Exemplary processes are well known in the art, and include, for example, sputtering, printing, etc. In a preferred embodiment, the electrodes and other conductive components are provided by coating a base substrate and then removing selected portions of the coating to yield the components. A preferred removal method is laser ablation, and more preferably broad-field laser ablation, as disclosed in the "Method of Making a Biosensor" application, which was incorporated above by reference, and further relevant discussion is found in U.S. patent application Ser. No. 09/866,030 (entitled "Biosensors with Laser Ablation Electrodes with a Continuous Coverlay Channel," filed May 25, 2001) and Ser. No. 09/411,940 (entitled "Laser Defined Features for Patterned Laminates and Electrode," filed Oct. 4, 1999). Various other methods of fabrication and application are well known in the art for providing the electrical components, and particularly the electrode systems, described herein.

Reagent Composition

The test strip includes a chemical reagent within the sample receiving chamber for reacting with the test analyte to produce the electrochemical signal that represents the presence of the analyte in the sample fluid. The test chemistry is selected in respect to the analyte to be assessed. As is well known in the art, there are numerous chemistries available for use with each of various analytes, including but not limited to the preferred chemistry described in patent application titled "Reagent Stripe for Test Strip" (attorney docket number 7404-566), which is being filed on even date herewith. The selection of an appropriate chemistry is therefore well within the skill in the art, and further description herein is not required in order to enable one to make and use the present invention.

For purposes herein, however, a preferred embodiment is described in which the analyte is glucose, although it is to be understood that the scope of the invention, and of the claims, is not so limited, unless specifically indicated. In the case of glucose, the active components of the test chemistry will typically include an enzyme for glucose and a redox mediator. The enzyme oxidizes glucose in the sample, and the mediator in turn reacts with the reduced enzyme. The mediator thereafter shuttles the redox equivalent of analyte product to the electrode surface by diffusion. There the mediator is oxidized quantitatively at a defined anodic potential and the resulting current is related to the apparent glucose concentration. There are a number of reagent systems suitable for the detection of glucose, and examples of these are contained in the AC Excitation, Analyte Sensors, and Biosensor applications, U.S. Pat. Nos. 5,385,846 and 5,997,817, and U.S. (Reissue) patent application Ser. No. 10/008,788 ("Electrochemical Biosensor Test Strip"), which are hereby incorporated by reference.

The glucose chemistry utilizes the redox mediator to mediate a current between the working electrode and the glucose analyte, which otherwise is not well suited for direct electrochemical reaction on an electrode. The mediator functions as an electron transfer agent that shuttles electrons between the analyte and the electrode. A great number of redox species are known and can be used as the redox mediator. In general, the preferred redox mediators are rapidly reducible and oxidizable molecules. Examples include ferricyanide, nitrosoaniline and derivatives thereof, and ferrocene and its derivatives.

Measurement Scheme

In one aspect of the present invention, a first pair of electrodes provides a first measurement that is combined with a second measurement obtained with a second pair of electrodes. As previously described, a conventional test strip employs at least two pairs of electrodes (each, e.g., a working electrode and a counter electrode) to determine the analyte concentration based upon the reaction of the analyte with a reagent located on or adjacent one of the electrode pairs. A basic measurement of the analyte concentration is thereby obtained. However, it is often desirable to correct or compensate that measurement for other factors, such as hematocrit, temperature, the presence of other species in the sample fluid, and the like. In one embodiment of the present invention, there is provided a biosensor and method which employs two pairs of electrodes, one to make the basic measurement of the analyte and the other to provide such correction or compensation for the basic measurement, in some instances to yield a final measurement figure.

The use of two pairs of electrodes may involve the use of disparate electrode sets, in which one pair comprises macro-electrodes and the other pair comprises micro-electrodes. As used herein, the term macro-electrode refers to an electrode whose primary effective diffusion characteristic is perpendicular to the surface of the electrode. Macro-electrodes are dimensioned and arranged so that the primary diffusion characteristics are linear diffusion characteristics. The term micro-electrode refers to electrodes exhibiting convergent, steady-state, or quasi-steady-state diffusion on the characteristic time scale of the measurement. A micro-electrode is an electrode to which radial diffusion provides a significant alteration in the response function. Micro-electrodes, for example, can be dimensioned and positioned such that their primary impedance characteristics are characteristic of edge-to-edge kinetics, e.g., between the nearest edges of the fingers. More of this functionality will be discussed with respect to the example embodiments shown in the drawings.

One advantage of using the micro-electrodes is that these devices can be configured and operated to very rapidly reach a quasi-steady state of current flux at the electrodes, for example in as little as 0.50 to 3.25 seconds, or even in less than one-half second. This rapid acquisition of quasi-steady state allows for a faster and more accurate determination of analyte concentration. This is contrasted with prior art approaches which have, for example, estimated or projected the result based on readings taken before a quasi-steady state is reached.

A further advantage seen in some embodiments of the invention is that the quasi-steady state response to application of a DC signal is at a higher magnitude than the quasi-steady state in many prior art systems. This improves the signal-to-noise ratio of the signal, thus enabling the system to provide a more accurate result.

A still further advantage seen with the interdigitated arrays of electrode fingers used in some forms of the present invention is the dramatically increased electrode edge length that can be achieved within a given space. Depending on the design, results can be derived in those systems with smaller samples, yet achieving the same quality of results as systems requiring larger samples.

It is noted that equations can be derived and used for the various micro-electrode configurations as would occur to those of ordinary skill in the art given this disclosure and the AC Excitation application, which was incorporated above by reference. It is also possible to use empirical measurements to directly determine the response function of the electrochemical structures present in each sensor design. It is noted that neither an analytic description of the response functions, nor attainment of a steady-state current are necessary for improved system performance.

General Description—Structure

The present invention provides electrode structures and systems that are useful in a wide variety of biosensor devices. Described herein are exemplary test strip configurations that demonstrate the utility of the present invention. It will be appreciated, however, that the principles of the present invention are equally applicable in various other biosensor designs. The particular compositions, sizes and other characteristics of the basic biosensor components are not critical and are therefore not limiting.

With reference to FIG. 1, generally, strip 210 has a first end 211 for communication with driving circuitry and metering circuitry (not shown), while end 218 is adapted to receive the bodily fluid in contact with electrodes as will be discussed herein. The driving circuitry provides a known current and/or potential through contacts 216 and monitors the current and/ or voltage response over a period of time. The respective signals travel between contacts 216 and the electrodes (shown in FIGS. 2-14) via conductors 270, 272, 274, and 276. These conductors are made of any, or a combination, of a variety of conductive materials, including for example gold or carbon, as would be understood by those skilled in the art.

Figure 2:
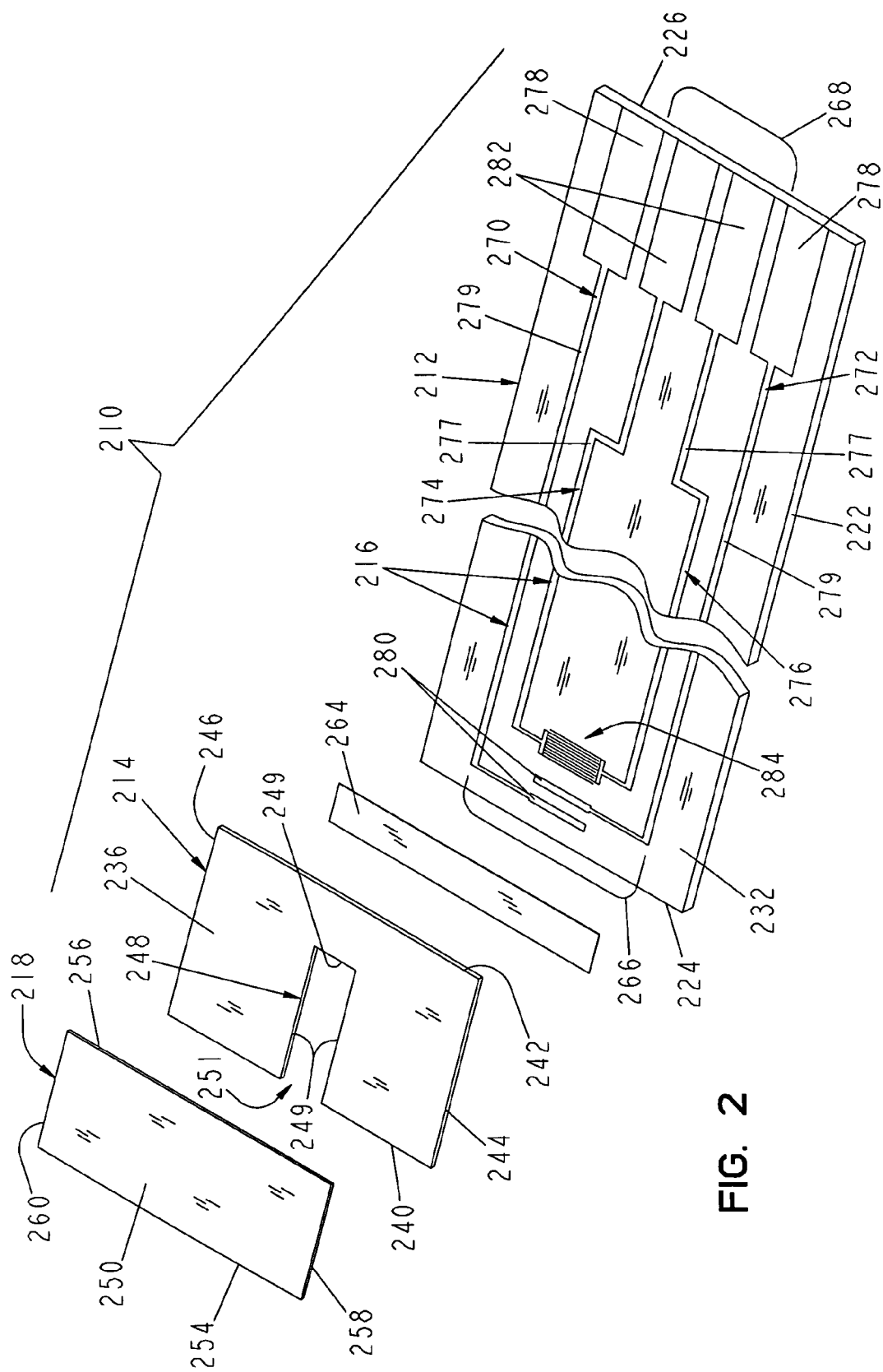
FIG. 2 is an exploded view of selected layers of the test strip of FIG. 1.

At end 218, notched fluid guide 214 is generally rectangular, with rectangular notch 148 cut therefrom, as can be seen in FIG. 2. Fluid guide 214 lies on the substrate layer 212 (a polyimide or other material, as disclosed in the "Method of Making a Biosensor" application, which was incorporated above by reference, or otherwise known in the art), and provides an opening 251 (see FIG. 2) for the fluid to be drawn from edge 224 toward vent 262 by capillary action. Cover layer 250 lies on top of guide layer 236 and provides an upper containment for the fluid path defined in part by notch 248. These structures will be discussed in more detail below.

Turning now to FIG. 2, with continuing reference to certain structures shown in FIG. 1, strip 210 includes substrate layer 212, reagent stripe 264, fluid guide 214, and cover layer 218. When assembled, passageway 248 is defined horizontally by inner notch surfaces 249, above by bottom surface 258 of cover layer 218, and below by reagent stripe 264 (which lies over electrode pair 284, but not over electrode pair 280) and electrode region 266 on upper substrate surface 232. During a testing operation, the fluid being tested enters passageway 248 through end 240 of fluid guide 214, past edges 254 and 224 of cover layer 218 and substrate 212, respectively. The fluid is drawn by capillary action into passageway 248, following a path extending away from edges 224 and 254, and toward vent 262 (see FIG. 1).

The capillary passageway provides a sample receiving chamber in which the measuring electrodes and associated reagent are contained, and the fluid sample containing the analyte contacts these components of the biosensor. It is a feature of the present invention that the dimensions of the capillary passageway may vary substantially. In one embodiment, the passageway is a volume that is 1000 µm wide, 100 µm high, and 2000 µm long. Other embodiments, and measurement of channels generally, are discussed in the Analyte Sensors application, referenced above. As the fluid travels along this path, it comes into contact with reagent and electrodes, as will be described in further detail below.

On substrate 212, contacts 278 are connected via traces 279 to electrodes 280. These electrodes 280 extend perpendicularly to the length of the substrate 212, parallel to edge 224 and to each other. In one preferred embodiment, electrodes 280 are rectangular, with a length sufficient to reach across the width of notch 248, a width of at least 50 µm, and a separation greater than about 50 µm between nearest points thereof. In another preferred embodiment, electrodes 280 are about 100 µm wide, with a 100 µm gap. In still other preferred embodiments, electrodes 280 are about 250 µm wide, with a 250 µm gap. Other configurations and dimensions will occur to those skilled in the art, and may be used in the present invention as required or desired given the design considerations for a particular strip and system.

Contacts 282 are connected via traces 277 to electrode pair 284. Electrodes 284 each comprise multiple, parallel, elongated rectangles ("fingers"), each extending approximately parallel to edge 224 and perpendicular to the center line of notch 248, reaching at both ends beyond the width of notch 248. The rectangles connect at one end or the other to trace 274 or 276 in an alternating pattern to form an interdigitated series of fingers, which will be discussed in further detail below. In various embodiments, each rectangular finger in micro-electrode pair 284 is between about 5 and about 75 µm in width, with a gap of about 5 to about 75 µm between adjacent fingers. The finger widths and the gaps between adjacent fingers are each preferably consistent across the width of notch 248.

Figure 3:
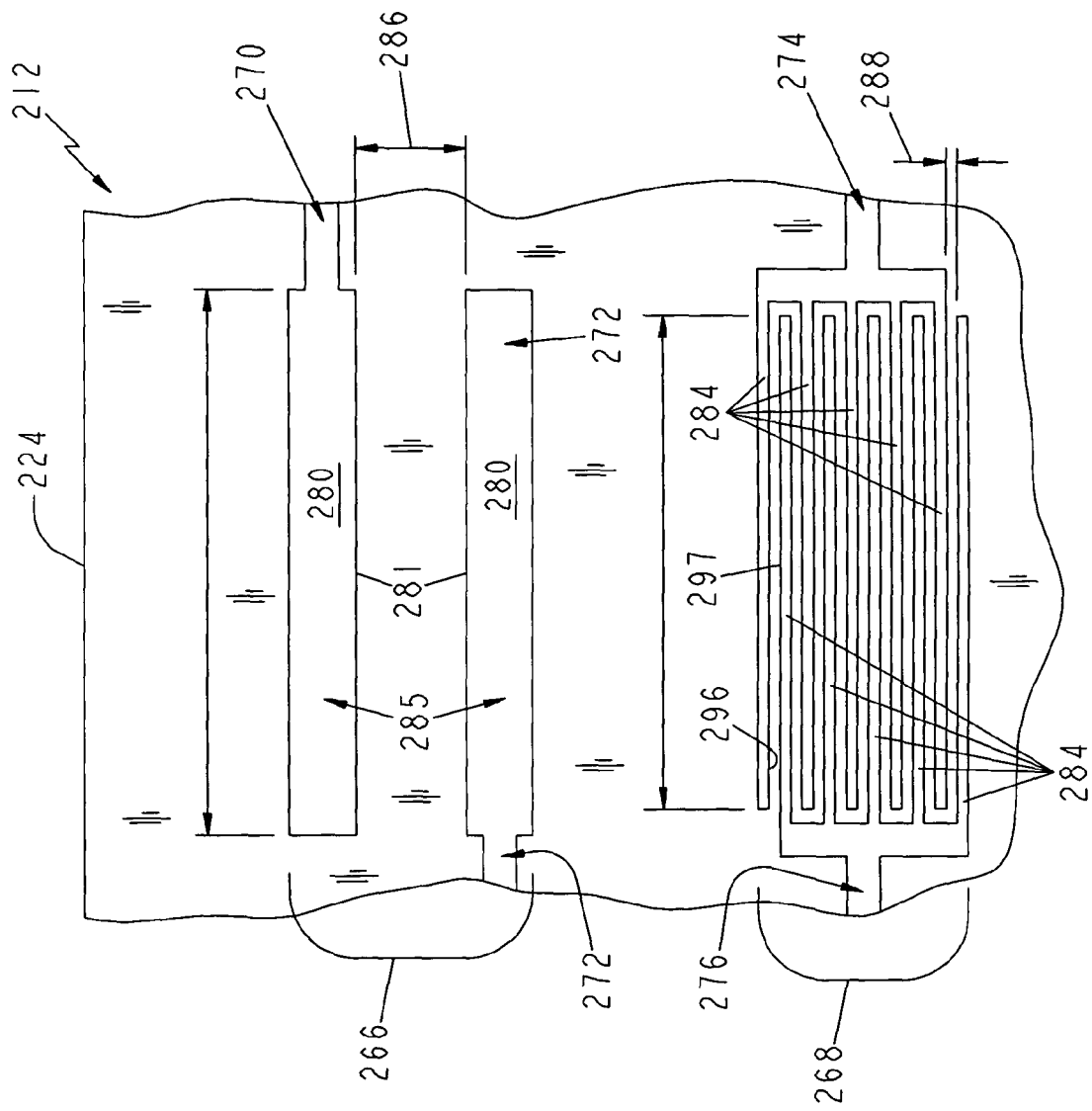
FIG. 3 is a cutaway plan view of the electrode portion of the strip of FIG. 1.

Turning now to FIG. 3, with continuing reference to FIG. 2, a more magnified view of the electrode portion of strip 210 in FIG. 2 is shown. As discussed above, electrodes 280 run parallel to edge 224 of strip 210, and connect to their conductive traces 270 and 272 at opposite ends, forming electrode pair 266. Their nearest edges 281 are separated by a distance ("gap") indicated by reference number 286 that is substantially constant throughout their length. Similarly, interdigitated fingers 284 form an electrode pair 268, with alternating fingers connecting to conductive traces 274 and 276.

Figure 4:
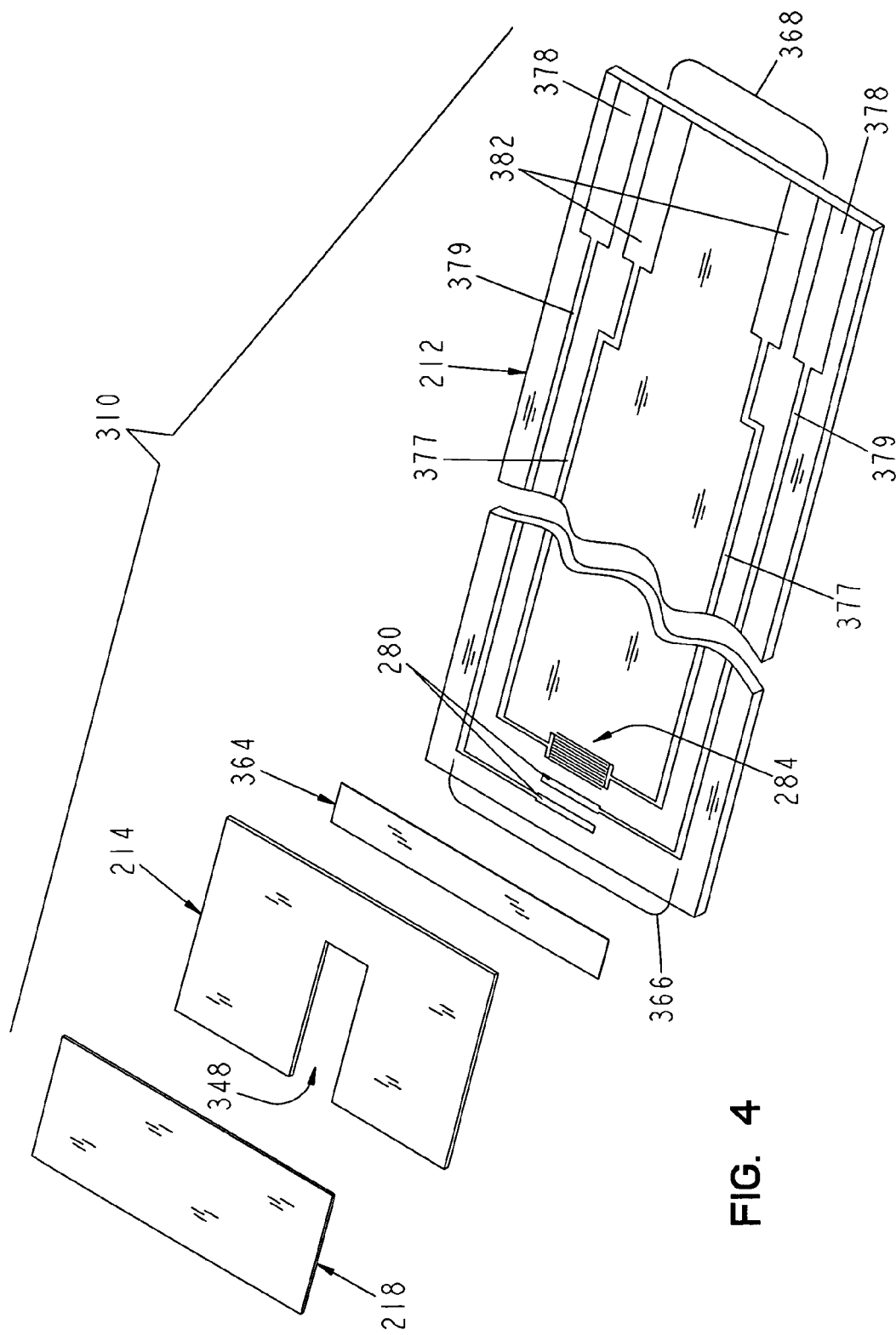
FIGS. 4-15 are exploded views of alternative test strips according to the present invention.

Turning to FIG. 4, strip 310 shows substrate layer 212, reagent stripe 364, notched fluid guide 214, and cover layer 218. In this embodiment, fluid entering capillary notch 348 defined by fluid guide 214 first encounters macro-electrodes 280. Macro-electrodes 280 are connected via conductors 379 to contacts 378 at end 368 of strip 310. Electrodes 280 are each, for example, about 250 µm in width, and the gap between them is also about 250 µm. Slightly further from strip end 366 is electrode pair 284, which is two electrodes of five fingers each, each finger on a side being connected via a conductor 377 to a contact 382 at strip end 368. Each finger in electrode pair 284 is a rectangle about 20 µm in width, and each adjacent finger is separated from the next by a gap of about 20 µm. Reagent stripe 364 covers electrode pair 280, but not electrode pair 284.

During a test, when the sample covers electrode pair 280, an AC signal is applied for a period of time to contacts 378. Similarly, for an overlapping period of time after the sample covers electrode pair 284, a DC signal is applied to contacts 382, and the electrical response between the electrodes in pair 284 is used to estimate the glucose concentration in the sample. The response of the sample between the fingers of electrode pair 280 is sensitive to the hematocrit of the sample, which along with a temperature value provided by a thermistor-based circuit provides a correction factor for the estimate obtained with electrodes 284. Note that this "correction factor" is not necessarily a multiplicative or additive factor, but may instead be used in a formula, in a lookup table, and/or in other ways to correct the estimate based on the temperature and the presence or absence of other materials in, or properties of, the sample as will be understood by those skilled in the art. See, for example, the AC Excitation application, which was incorporated above by reference. In this embodiment, the volume of blood within capillary notch 348 sufficient to cover the measuring electrodes is about 130 nL.

Figure 5:
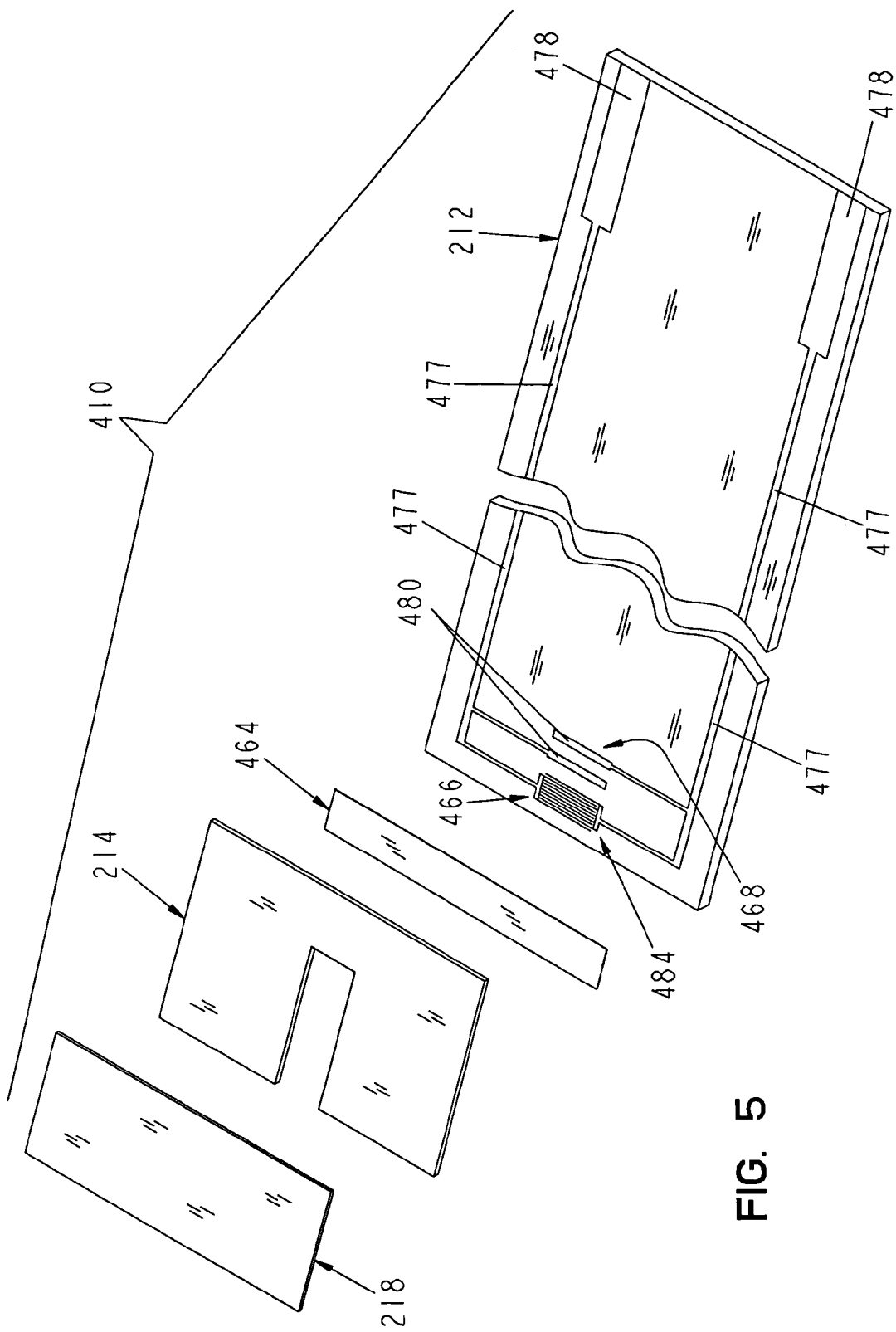

An alternative embodiment is shown in FIG. 5 as strip 410. Substrate layer 212 is traced with two contacts 478, and is partially covered with reagent stripe 464 (over electrodes 480), notched fluid guide 214, and cover layer 218. Contacts 478 are electrically connected via conductive traces 477 to both a first pair of electrodes 466 and a second pair of electrodes 468, one electrode from each pair being connected on each side to one of contacts 478. Note that in this embodiment the driver and meter circuitry (not shown) uses a single pair of contacts 478 to drive and measure response from both pairs of electrodes. Note further that the relative placements of micro-electrodes 484 and macro-electrodes 480 are reversed relative to the embodiment shown in FIG. 4. The macro-electrodes 480 are again, for example, about 250 µm in width with a gap of about 250 µm between them. Also, each electrode in micro-electrode pair 466 is made of five fingers that are interdigitated with the fingers in the other electrode of the pair. Each finger is again about 20 µm in width with a gap of about 20 µm between neighboring fingers.

In this embodiment, reagent stripe 464 covers electrode pair 468, but not electrode pair 466. When the sample covers electrode pair 466, the system uses an AC signal through that pair to determine correction factors for the analyte measurement. When the sample has covered electrode pair 468, an estimate of the analyte concentration is obtained using DC excitation methods known in the art, such as U.S. patent application Ser. Nos. 09/530,171 and 10/264,891, PCT Application Number (WO) US98/27203, U.S. Pat. No. 5,997, 817, and the Electrochemical Biosensor Test Strip (reissue) application. With the exemplary dimensions described above, the volume of the capillary cavity is about 130 nL.

Figure 6:
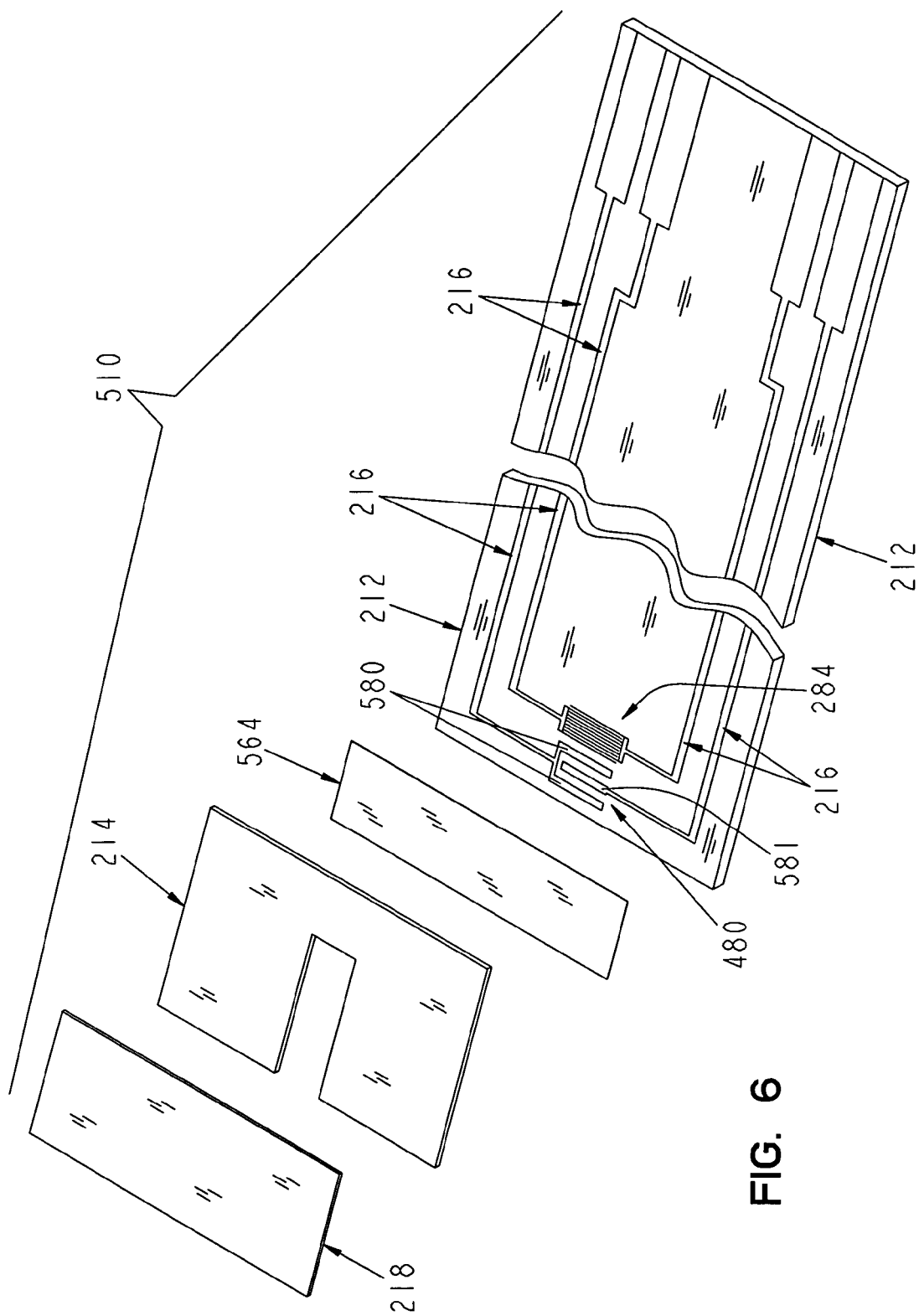

Turning now to FIG. 6, it can be seen that strip 510 again comprises substrate layer 212, reagent stripe 564, notched fluid guide 214, and cover layer 218. In this embodiment, working electrode 581 lies between two counter electrode fingers 580, which are connected by one of the conductors 216 to the same contact. These electrodes 580 and 581 form a first electrode pair 480, and each of the three macro-electrode fingers in this electrode pair 480 is about 250 µm wide, with a gap of about 250 µm on either side of working electrode 581.

Second electrode pair 284 comprises two electrodes of six and seven fingers each, respectively, the fingers being interdigitated in an alternating pattern. Each finger is again about 20 µm wide, with a gap of about 20 µm between adjacent fingers. In this embodiment, the reagent layer 564 covers both electrode pairs 480 and 284. The macro-electrode pair 480 provides Cottrell-like response, where current is proportional to the square root of the diffusion coefficient, while the micro-electrode pair 284 provides current that is directly proportional to the diffusion coefficient. The two responses, taken together, correct for environmental factors to yield an improved response. The volume of sample required for measurement in this embodiment is about 200 nL.

Figure 7:
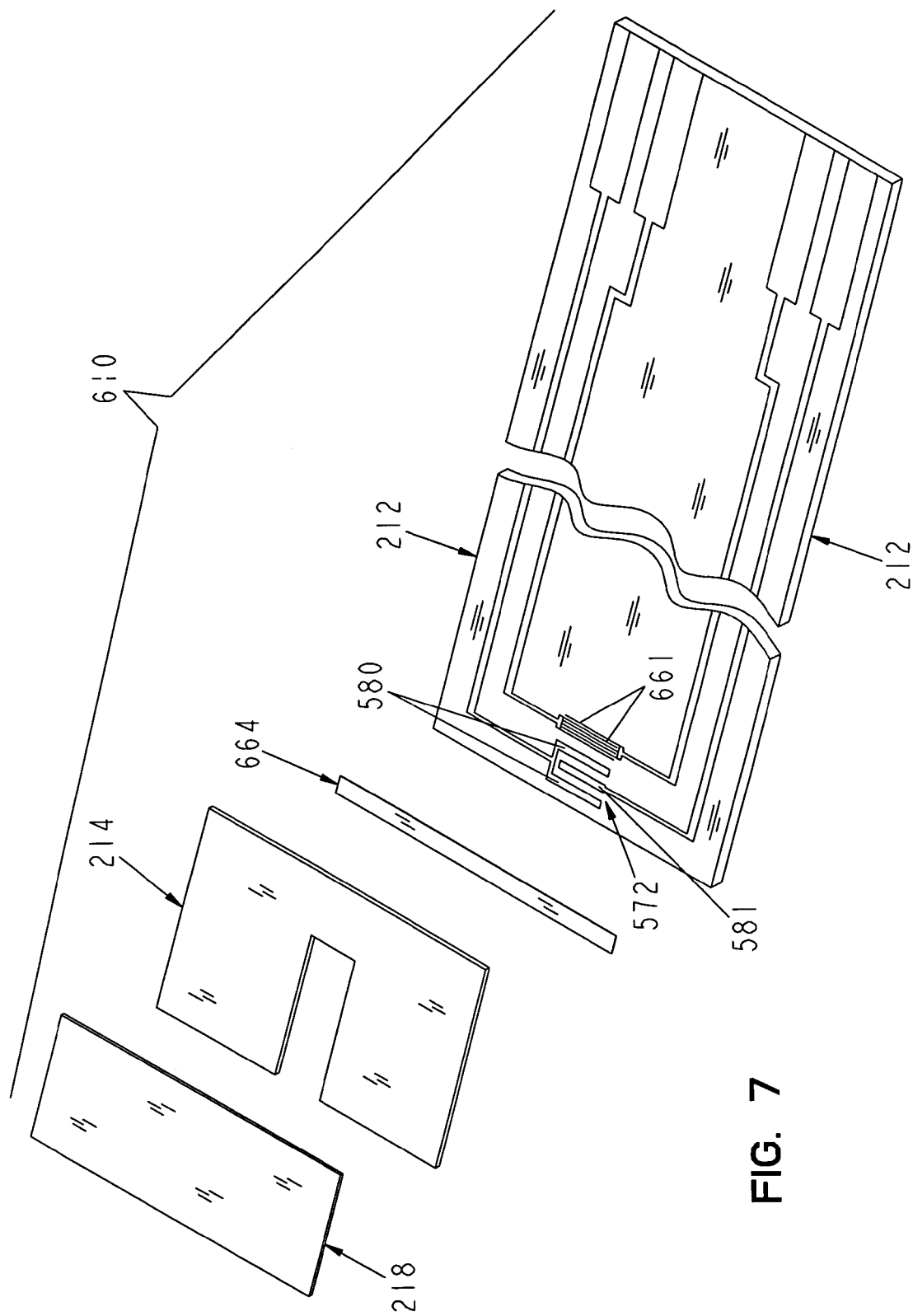

Another alternative embodiment is shown in FIG. 7. Strip 610 comprises substrate layer 212, reagent stripe 664, notched fluid guide 214, and cover layer 218. As in FIG. 6, the first electrode pair 572 comprises counter and working macro-electrodes 580 and 581, respectively, each about 250 µm wide with a gap of about 250 µm between them. In this embodiment, however, electrode pair 661 comprises two electrodes of three fingers each. Each finger is about 50 µm in width, with a gap of about 50 µm between adjacent fingers.

The first electrode pair that the sample reaches (the macro-electrode pair 572) is used to obtain a hematocrit-based measurement using AC excitation techniques. The second electrode pair (the micro-electrodes 661) is used to obtain a measurement that depends on the glucose in and hematocrit of the sample using DC excitation. The reagent stripe 664 covers only electrode pair 661, and a sample volume of about 200 nL is required to fill the capillary volume in the relevant region. The measurements are combined as parameters to a formula based on the electrode configuration, reagent system, and other factors as would occur to one of skill in the art.

Figure 8:
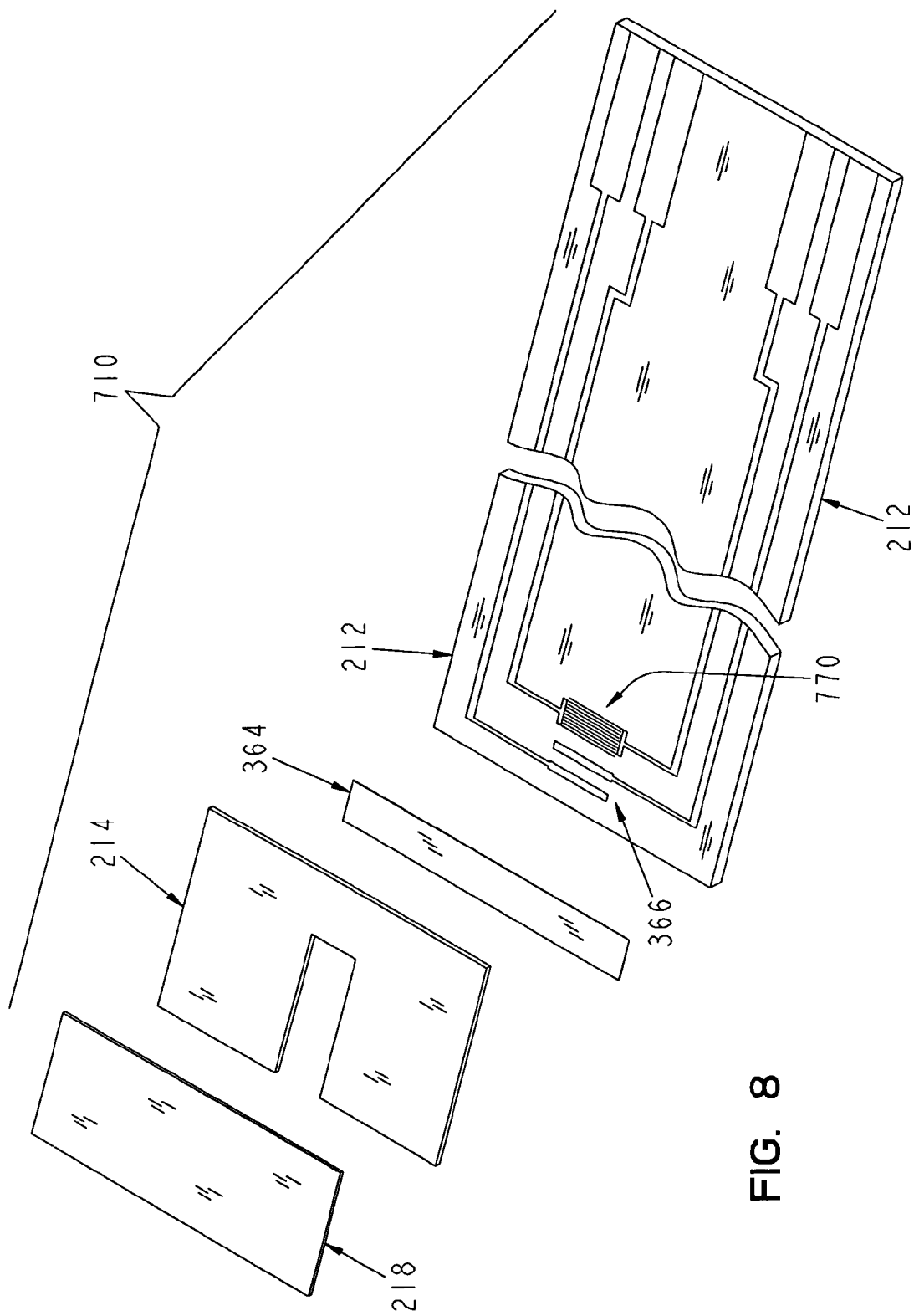

FIG. 8 provides yet another embodiment of the present invention. Strip 710 comprises substrate layer 212, reagent stripe 364, notched fluid guide 214, and cover layer 218. In this embodiment, first electrode pair 366 comprises two macro-electrodes, each having a single rectangular finger, while second electrode pair 770 comprises two micro-electrodes, each micro-electrode having five fingers in an interdigitated pattern. The fingers in this embodiment are about 50 µm wide, with a gap of about 30 µm between them, and reagent stripe 364 covers second pair 770. The volume necessary to cover the electrodes in the relevant portion of the capillary path is about 170 nL.

Figure 9:
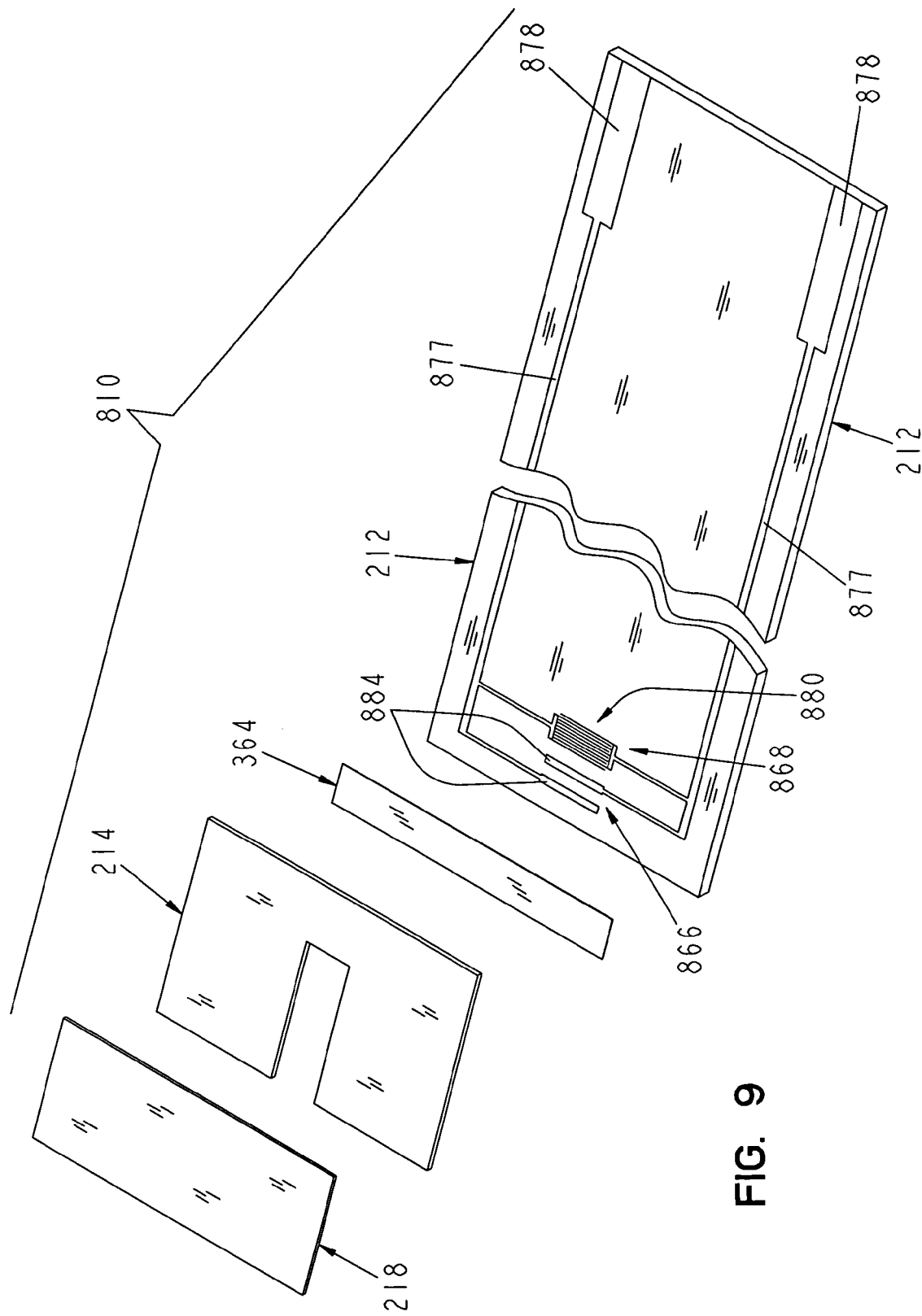

Turning now to FIG. 9, strip 810 comprises substrate layer 212, reagent stripe 364, notched fluid guide 214, and cover layer 218. A single pair of contacts 878 is connected via conductors 877 to both first electrode pair 866 and second electrode pair 868. First electrode pair 866 comprises two single-finger macro-electrodes 884, while second electrode pair 868 comprises two micro-electrodes 880, each micro-electrode having five fingers in an interdigitated pattern. Each electrode in first electrode pair 866 is again about 250 µm wide, with a gap of about 250 µm between them. First electrode pair 866 is used to obtain a first measurement based on the hematocrit of the sample. Each finger of the second pair 868 is about 50 µm wide with a gap of about 30 µm between adjacent fingers. When the sample covers second electrode pair 868, a DC signal is applied to contacts 878. The resulting impedance between electrodes 868 is used to obtain a second measurement based on the concentration of glucose in and hematocrit of the sample. That measurement is combined in a formula with the measurement obtained through first electrode pair 866 and a temperature signal from a thermistor (not shown) to obtain a corrected glucose concentration value. Reagent stripe 364 covers second electrode pair 868, and the required volume of sample is again about 170 nL.

Figure 10:
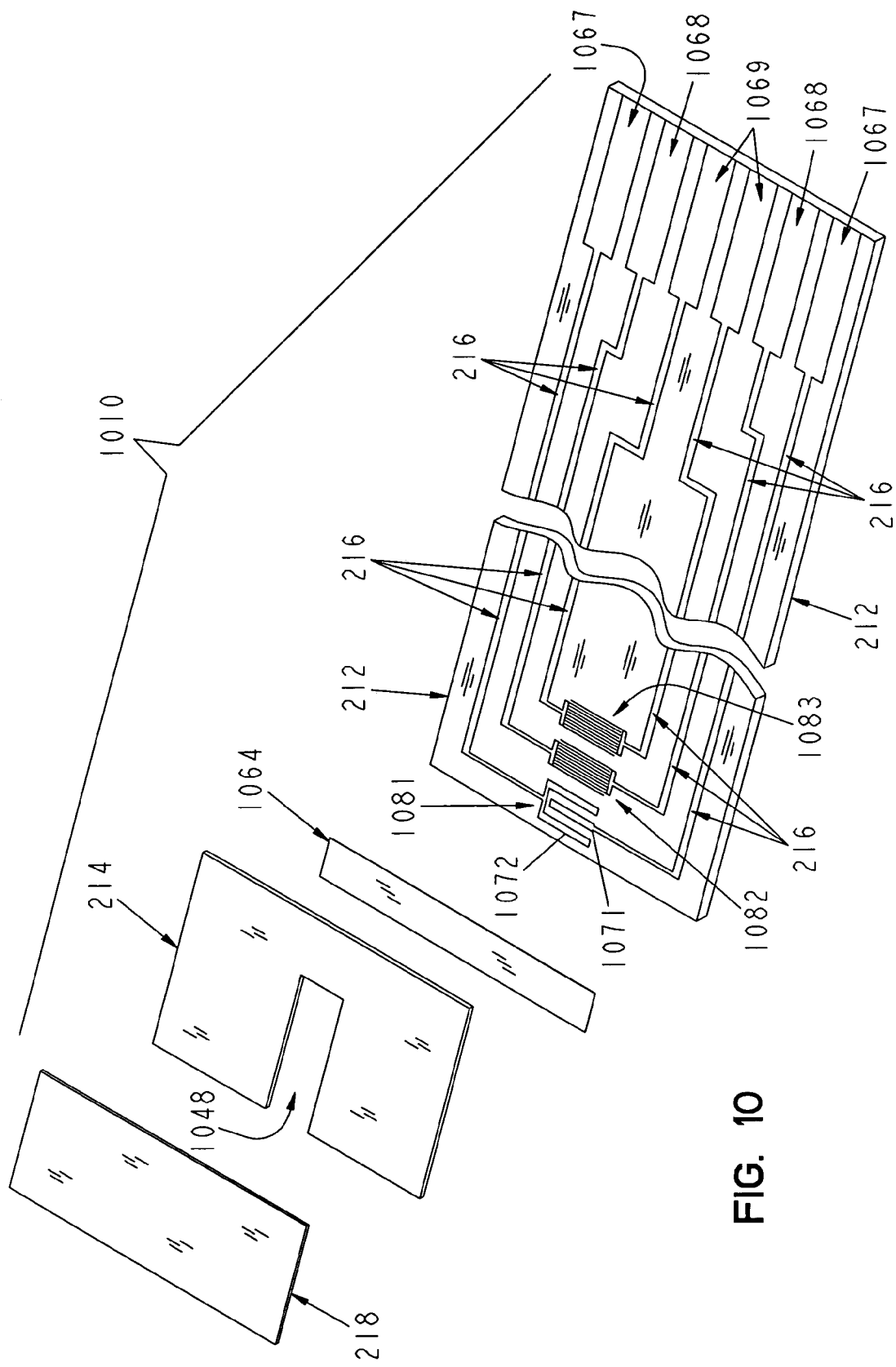

FIG. 10 shows another alternative embodiment, strip 1010, which comprises substrate layer 212, reagent layer 1064, notched fluid guide 214, and cover layer 218. In this embodiment, the first electrode pair 1081 encountered by the sample includes working electrode 1071, a single-finger electrode. First electrode pair 1081 also includes counter electrode pair 1072, a two-finger electrode, with one finger on either side of working electrode 1071. Each finger in first electrode pair 1081 is about 250 µm wide, and a gap of about 250 µm separates each counter electrode finger from the working electrode finger. Each of the electrodes (i.e., working electrode 1071 and counter electrode 1072) in first electrode pair 1081 is electrically connected via a conductive trace 216 to a contact 1067. The system driver connects to contacts 1067 to use the first electrode pair to obtain an estimated concentration of analyte in the sample.

The second electrode pair 1082 comprises two electrodes of five fingers each. These fingers are each about 50 µm wide with a separation of about 30 µm between them. Each electrode in the second pair connects to a conductive trace 216 to be electrically connected to a contact 1068, which contacts are used to drive and measure for correction factors such as hematocrit based on the analyte interaction with the second pair of electrodes.

The third electrode pair 1083 is also a micro-electrode configuration, with each of the two electrodes in the third pair 1083 having five fingers interdigitated with the five in the other electrode. Each finger is again about 50 µm wide, with a gap of about 30 µm between them. Each electrode in the third pair 1083 is connected via a conductive trace 216 to a contact 1069, and is driven via those contacts to detect sufficiency of the sample volume, based on the electrical response between those electrodes when the sample has reached a sufficient extent through the sample cavity 1048. Note that reagent layer 1064 covers upstream electrode pair 1081 in this embodiment. The sample cavity in this embodiment requires about 220 nL of sample fluid to cover all three electrode pairs.

Figure 11:
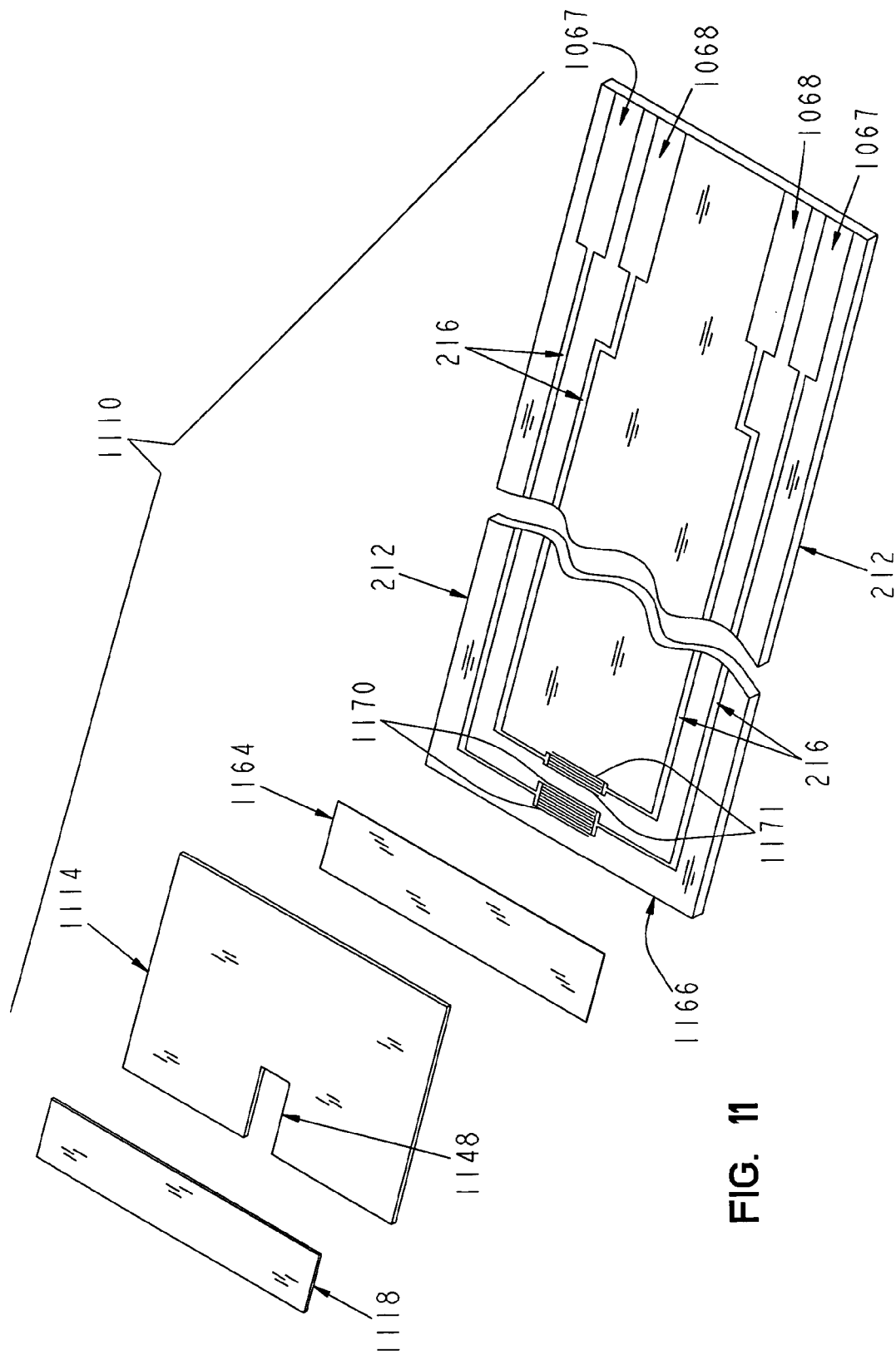

Turning now to FIG. 11, strip 1110 comprises substrate layer 212, reagent stripe 1164, notched fluid guide layer 1114 with notch 1148, and cover layer 1118. The first electrode pair 1170 from the sample end 1166 of strip 1110 comprises two electrodes of five fingers each, where each finger is about 20

μm wide, and a gap of about 20 μm separate each adjacent finger. This electrode pair is used for determining the concentration of interferents such as hematocrit by using AC excitation and impedance measurement techniques. For an example of these techniques, see the AC Excitation application, which was incorporated above by reference.

The second electrode pair 1171 from sample end 1166 of strip 1110 comprises two electrodes of three fingers each. Each finger is about 20 μm wide, and a gap of about 20 μm separating adjacent fingers. This system derives a temperature-compensated estimate of glucose concentration by applying AC or DC excitation techniques to this second electrode pair 1171. The sample volume required to fill the capillary channel and cover the electrodes in this embodiment is about 69 nL.

Figure 12:
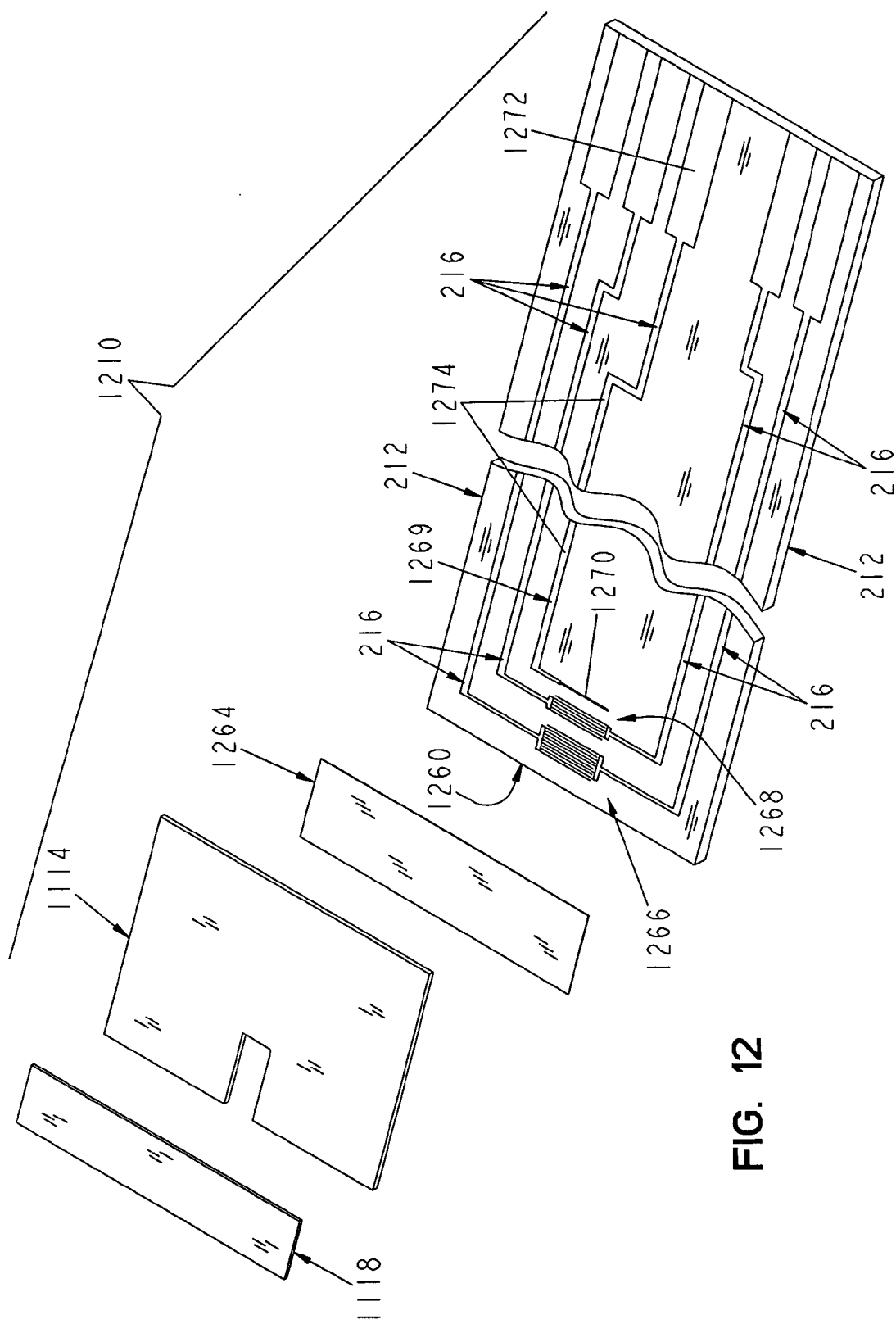

Turning now to FIG. 12, strip 1210 comprises substrate 212, reagent stripe 1264, notched fluid guide 1114, and cover layer 1118. The first electrode pair 1266 from the sample end 1260 of strip 1210 includes two electrodes of five fingers each. This system uses the first pair of electrodes 1266 in strip 1210 to obtain one measurement based in substantial part on detection of interferents for combining with, another measurement, which is obtained using the second electrode pair 1268. The second electrode pair from the sample end of strip 1210 is electrode pair 1268, which includes two electrodes, each having three fingers, and the pair 1268 is covered by reagent layer 1264. The fingers in second electrode pair 1268 are also about 20 μm wide and are separated by a gap of about 20 μm. This second electrode pair 1268 is used by the system to estimate the concentration of the analyte in the sample. While the first electrode pair 1266 implements AC techniques, the second electrode pair 1268 is driven by an AC or DC signal. Further downstream from the sample end (beyond the second electrode pair 1268) is third electrode 1270, which is a single electrode finger about 20 μm wide, connected via conductor 1274 to contact 1272. The AC signal response between this third electrode 1270 and either the first electrode pair 1166 or the second electrode pair 1168 provides a sample sufficiency signal for the system. In a variation of this embodiment, third electrode 1270 operates as an electrode in a circuit with second electrode pair 1168, for application of various detection and measurement techniques known in the art.

Figure 13:
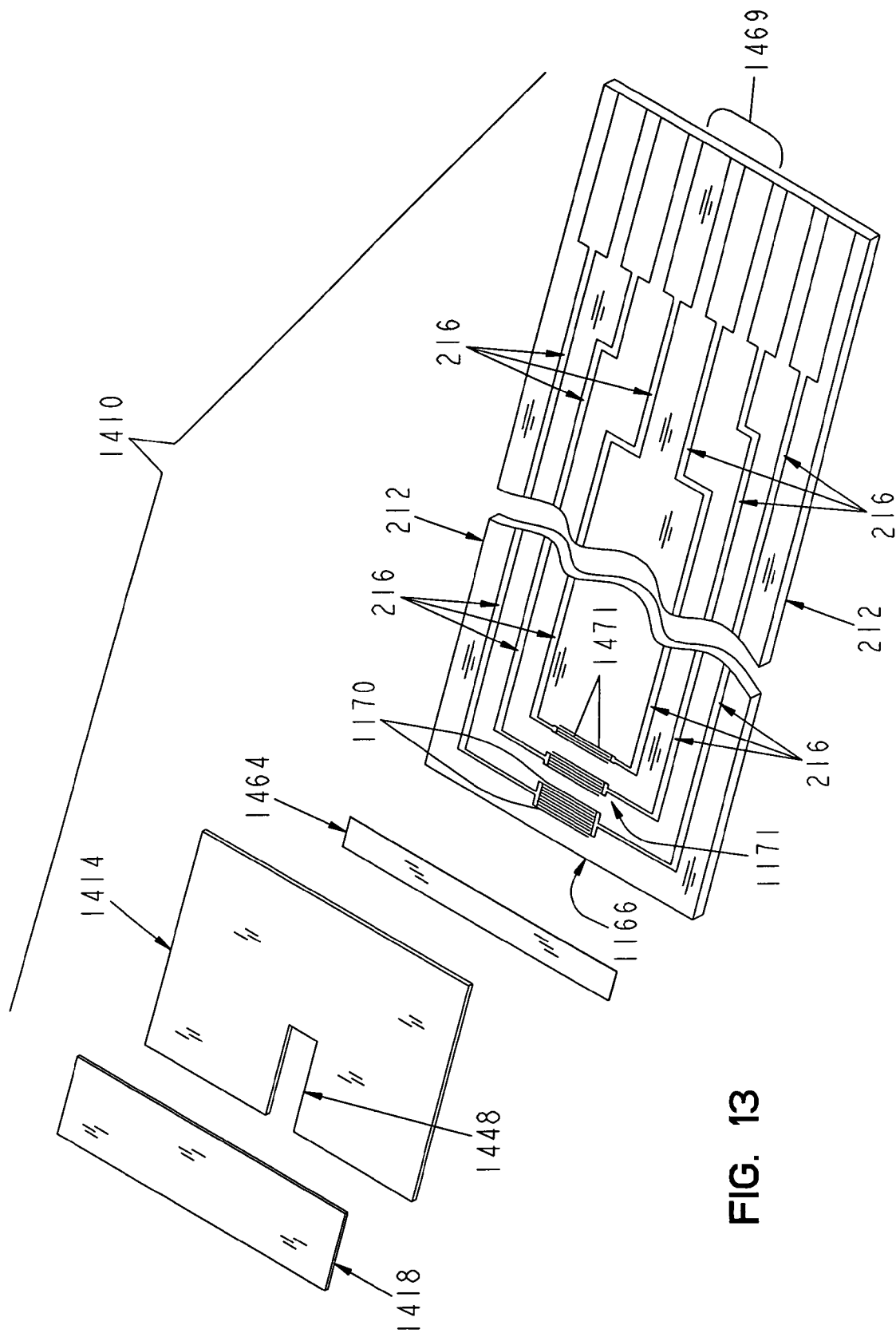

FIG. 13 shows strip 1410, which comprises substrate 212, reagent stripe 1464, fluid guide 1414 with notch 1448, and cover layer 1418. The first set of electrodes 1170 from the sample end 1166 of strip 1410 includes two electrodes, each having five fingers. The fingers in electrodes 1170 are each about 20 μm wide, with a gap of about 10 μm separating adjacent interdigitated fingers.

Second set of electrodes 1171 comprises two electrodes having three fingers each. The fingers of electrodes 1171 are each about 20 μm wide, with a gap of about 10 μm between adjacent, interdigitated fingers. While the first electrode pair 1170 is used by the system to determine the hematocrit of the sample and calculate a correction factor, an estimate of the glucose concentration is derived from the response of the second set of electrodes 1171 in the presence of the sample and reagent. The third pair of electrodes 1471 is two electrodes having two fingers each. In this embodiment, a potential is applied across the third pair 1471 until the sample reaches the pair, thus changing the impedance presented between the electrodes. The system can then conclude that the sample has sufficiently covered the first set 1170 and the second set 1171 of electrodes for an accurate analysis to be made. A sample volume of about 63 nL is required to cover the three sets of electrodes in this exemplary embodiment.

Figure 14:
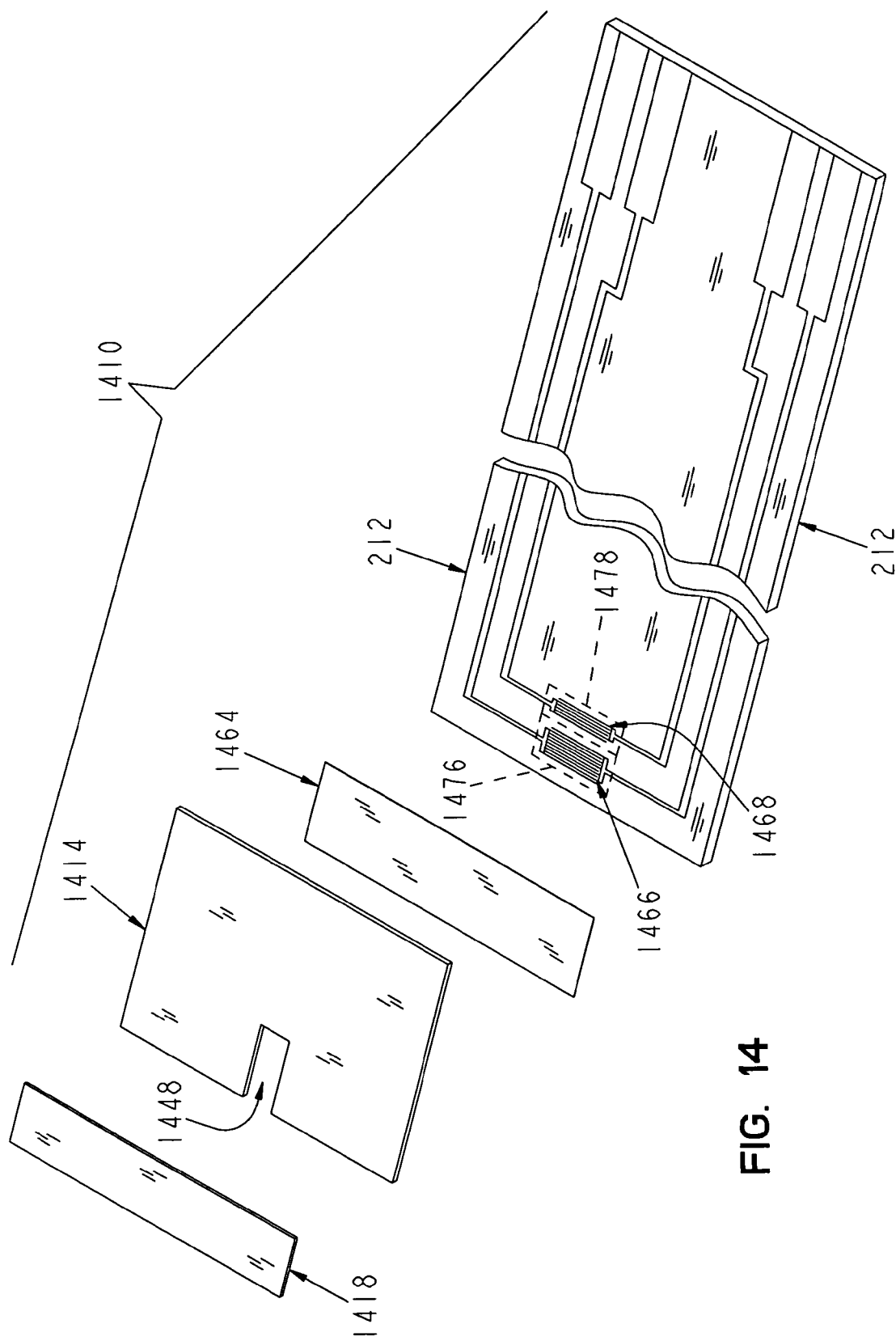

FIG. 14 shows strip 1410, having substrate layer 212, reagent stripe 1464, notched fluid guide 1414 (with notch 1448), and cover layer 1418. The first electrode pair 1466 defines a first sensing zone 1476, and comprises two electrodes of five fingers each. The fingers are about 20 μm across, and include a gap of about 20 μm between interdigitated fingers. This pair 1466 is used to provide a response that reflects the hematocrit of the sample, allowing the system to correct the estimated concentration of glucose in the sample as determined by using the second pair of electrodes 1468. The second pair of electrodes 1468 defines second sensing zone 1478, and includes two electrodes having three fingers each. The finger sizes and gaps for second electrode pair 1468 are the same as those for first electrode pair 1466. Second electrode pair 1468 is used to obtain correction factors for the concentration estimate obtained by the first electrode pair 1166, and uses AC/impedance measurement techniques.

Figure 15:
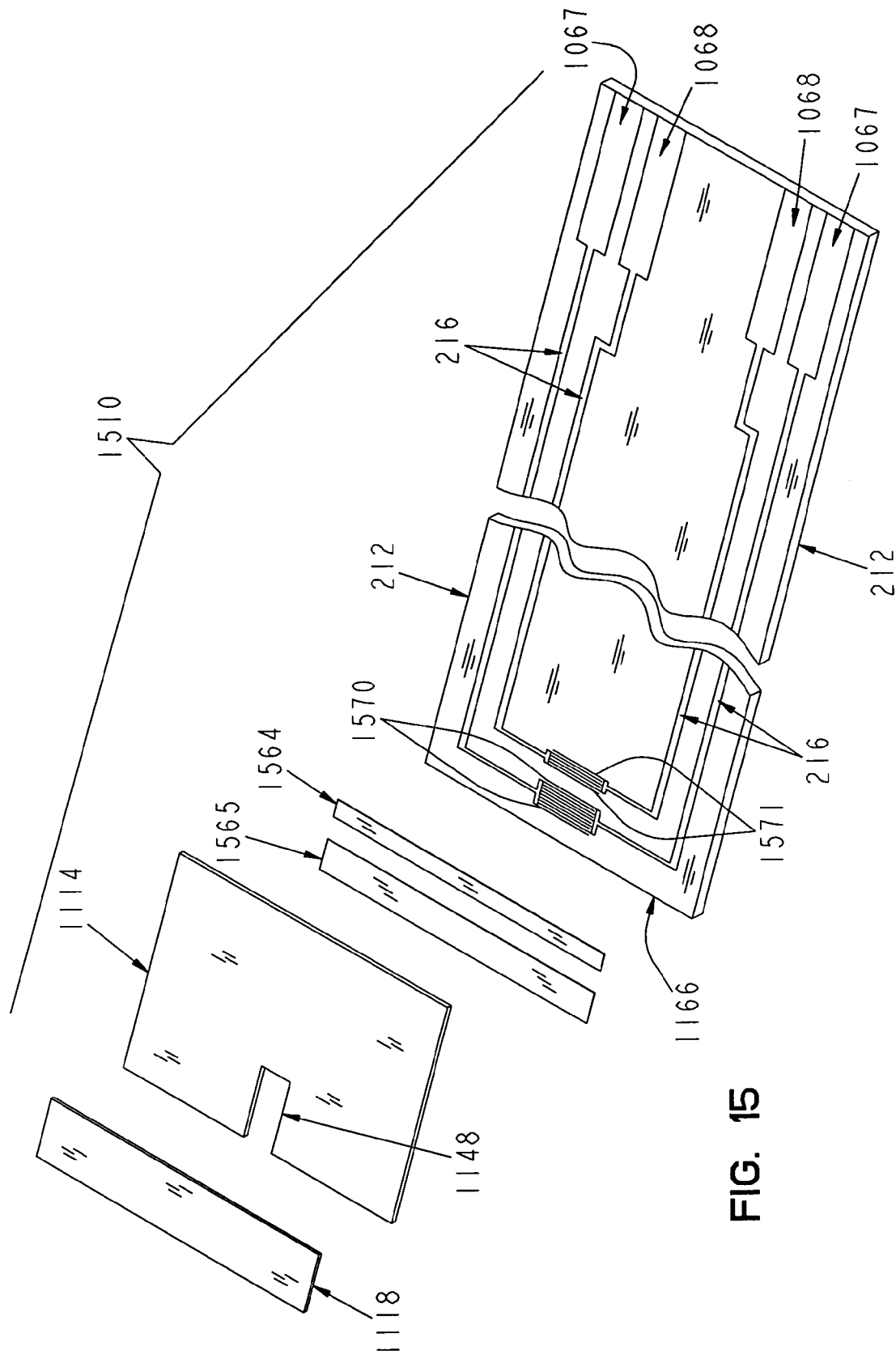

FIG. 15 shows strip 1510, a variation of the strip in FIG. 11, where electrode pairs 1570 and 1571 and the layers covering them would be slightly modified. In particular, electrode pair 1570 comprises a working electrode having four fingers, each 50 μm wide with a gap width of 20 μm. The corresponding counter electrode in electrode pair 1570 has three fingers, also 50 μm wide. The second electrode pair 1571 comprises a working electrode having two fingers, each 100 μm wide, and a counter electrode having a single finger that is also 100 μm wide, with a gap width of 20 μm. In this embodiment, reagent 1564 would cover only electrode pair 1571, while coating 1565 would cover electrode pair 1570. Coating 1565 is a perm-selective, size-selective, ion-selective, or other coating that limits the portions or components of the sample that affect the measurement at electrode pair 1570, as are well known in the art. In variations on this embodiment, three or more electrode pairs would be present, and each electrode pair would be covered with a different reagent or other coating, or combination of coatings to provide a corresponding number of measurements with different sensitivities, which measurements would be combined to determine the final measurement output. In other respects, except constants and functions derived from the cell geometry and the selection of coating 1565 and reagent 1564, measurement occurs as described in relation to FIG. 11.

Various aspects of the described embodiments can be combined as desired or necessary, according to the design parameters and preferences for a given system. For example, there may be a one-to-one correspondence between electrodes and contacts on a strip, as shown, for example, in FIG. 4. Alternatively, all electrodes whose fingers are combined on the same side of a strip may be electrically connected to the same contact, as shown for example, in FIG. 5, providing a many-to-one relationship.

Furthermore, any design discussed herein can accommodate one or more "dose sufficiency" electrodes downstream from those used to analyze the sample, as shown in FIGS. 11 and 14. Such dose sufficiency electrodes might comprise two or more electrodes, and the associated circuitry could determine whether the sample has reached those electrodes based on the impedance presented between them. Alternative embodiments include a single dose sufficiency electrode, and the meter and driver circuitry use the impedance between it and a measuring electrode (working or counter-electrode, estimating or correcting pair) to detect the presence of the sample fluid in the space between those electrodes.

As previously described, the biosensor may similarly include a dose detection electrode system that is comparable to the dose sufficiency electrode system except that it is located closer to the edge of the test strip, upstream of the measuring electrodes as the sample enters the test strip. Such a dose detection electrode system may include a single electrode that operates in combination with the measurement or other electrodes separately provided. Alternatively, the dose detection electrode system may include a pair of electrodes which cooperate with one another to indicate when a sample fluid has bridged the gap between the dose detection electrodes. The dose detection electrodes are therefore seen to be analogous to the dose sufficiency electrodes in terms of operation, but differ as to the location of the electrodes in their upstream position relative to the measurement electrodes.

In other variations, a thermistor in the system is used to determine the temperature, which is used along with the hematocrit reading to correct the glucose estimate. In others, the second pair of electrodes provides a temperature-compensated glucose estimate using techniques known to those skilled in the art.

In still other variations, the pair of electrodes that the sample first encounters is a pair of macro-electrodes, while in others, it is a micro-electrode pair. In either case, each electrode comprises 1, 2, 3, 4, 5, or more fingers of appropriate dimension, all electrically connected both to each other and to a contact for communication with the meter/driver electronics.

Yet further variations use other combinations of measurements to achieve desired results. Generally, these variations apply electrical signals to two or more electrodes to obtain a corresponding number of response signals. Because of the difference in the signal (AC versus DC, spectrum, amplitude, and the like), electrode shape or dimensions, reagent applied to the sample (or possibly the lack of reagent at one or more electrodes), and/or other differences, the response signals are sensitive to different combinations of analyte concentration and interferents. In one such example, a first response is correlated with the hematocrit of the sample, while a second response is correlated with a combination of hematocrit and concentration of glucose in the sample. In another such example, a first response is correlated with temperature, a second response is correlated with a combination of temperature and hematocrit, and a third response is correlated with a combination of temperature, hematocrit, and glucose. The result function(s) are likely to vary for each design, but they can be determined empirically by those skilled in the art without undue experimentation.

Those skilled in the art will appreciate that, while the embodiments herein have been described in terms of combining measurements, or taking a measurement and determining a correction factor, systems according to the present invention can use any suitable geometry and any appropriate technique to obtain and combine the plurality of measurements to achieve the final detection or measurement result. That is, those practicing this invention may use more or fewer electrodes, and any formula to combine readings that is suitable in light of the geometries, reagents, and other system design choices made in connection with that design.

As discussed in the Analyte Sensors application, which was incorporated above by reference, accurate detection of analytes can be achieved in a smaller-volume strip-based system according to the present invention, without detrimental impact to the connector, than in prior art systems. This allows a smaller sample to suffice for measurement, saving time and hassle for users of the system.

All publications, prior applications, and other documents cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that would occur to one skilled in the relevant art are desired to be protected.

What is claimed is:

1. In a test strip for measuring the concentration of an analyte in a bodily fluid, the test strip defining a capillary passageway, the passageway being dimensioned so as to induce movement of a sample of bodily fluid along a predetermined path through the passageway extending inwardly from an entrance at an edge of the test strip, the improvement comprising:
   providing a first set of electrodes in electrical communication with the passageway, the first set of electrodes including at least two electrodes separated by a distance of less than 50 µm;
   providing a second set of electrodes in electrical communication with the passageway, the second set of electrodes including at least two electrodes separated by a distance greater than 50 µm; and
   a reagent located within the capillary passageway, the reagent combining with the bodily fluid to produce a redox reaction,
   said reagent being located over at least one of the first and second sets of electrodes, and
   the other of the first and second sets of electrodes either having said reagent located thereover or having no reagent located thereover.

2. The test strip of claim 1, wherein the second set of electrodes comprises a pair of electrodes with substantially parallel, interdigitated fingers, each electrode having at least two fingers, and each of the fingers being greater than 50 µm from the nearest other finger in the second set of electrodes.

3. The test strip of claim 2, wherein the first set of electrodes comprises a pair of electrodes with substantially parallel, interdigitated fingers, each of the fingers being less than 50 µm from the nearest other finger in the first set of electrodes.

4. The test strip of claim 3, wherein each of the fingers is at least 1 µm from the nearest other finger in the first set of electrodes.

5. The test strip of claim 3, wherein each of the fingers is at least 10 µm from the nearest other finger in the first set of electrodes.

6. The test strip of claim 1, wherein the first set of electrodes comprises a pair of electrodes with substantially parallel, interdigitated fingers, each electrode having at least two fingers, and each of the fingers being less than 50 µm in width.

7. The test strip of claim 6, wherein the first set of electrodes comprises a pair of electrodes with substantially parallel, interdigitated fingers, each electrode having at least two fingers, and each of the fingers being less than 50 µm in width.

8. The test strip of claim 6, wherein each of the fingers of the first set of electrodes is at least 1 µm from the nearest other finger in the first set of electrodes.

9. The test strip of claim 8, wherein each of the fingers of the first set of electrodes is at least 10 µm from the nearest other finger in the first set of electrodes.

10. The test strip of claim 1, further comprising a third electrode system in electrical communication with the passageway for determining when a sample has entered a predetermined distance into the passageway.

11. The test strip of claim 10, wherein the third electrode system includes an electrode that is closer to the entrance of the passageway than both the first set of electrodes and the second set of electrodes.

12. The test strip of claim 11, wherein the single electrode has one or more electrically connected fingers, each finger having a width between 5 μm and 50 μm.

13. The test strip of claim 10, wherein the third electrode system comprises a first dose detect electrode and a second dose detect electrode, both of which are closer to the entrance of the passageway than both the first set of electrodes and the second set of electrodes.

14. The test strip of claim 13, wherein each of the dose detect electrodes has a plurality of electrically connected fingers, each finger being substantially rectangular in shape and having a width between 5 μm and 50 μm.

15. The test strip of claim 1, further comprising a third electrode system in electrical communication with the passageway for determining when a sample has filled the passageway to cover the first set of electrodes and the second set of electrodes.

16. The test strip of claim 15, wherein the third electrode system includes an electrode that is farther from the entrance of the passageway than both the first set of electrodes and the second set of electrodes.

17. The test strip of claim 16, wherein the electrode that is farther from the entrance of the passageway than both the first set of electrodes and the second set of electrodes has one or more electrically connected fingers, each finger being substantially rectangular in shape and having a width less than 50 μm.

18. The test strip of claim 15, wherein the third electrode system comprises a sample sufficiency working electrode and a sample sufficiency counter electrode, both of which are farther from the entrance of the passageway than both the first set of electrodes and the second set of electrodes.

19. The test strip of claim 18, wherein the sample sufficiency working electrode and the sample sufficiency counter electrode each have a plurality of electrically connected fingers, each finger being substantially rectangular in shape and having a width between 5 μm and 50 μm.

20. The test strip of claim 1, wherein: the first set of electrodes comprises a first electrode and a second electrode; the second set of electrodes comprises a third electrode and a fourth electrode; the first electrode and the third electrode are electrically connected to each other; and the second electrode and the fourth electrode are in electrical communication with each other.

21. A diagnostic strip for measuring the concentration of an analyte in a bodily fluid, the test strip defining a capillary passageway, the passageway being dimensioned so as to induce movement of a sample of bodily fluid along a predetermined path through the passageway extending inwardly from an entrance at an edge of the test strip, comprising:
a first electrode pair, comprising a first electrode and a second electrode, operating in a first substantially planar physical zone, the first electrode and the second electrode each including a plurality of fingers, the fingers of the first electrode and the second electrode being interdigitated and being separated from their nearest adjacent fingers by at most 50 μm at their nearest points;
a second electrode pair, comprising a third electrode and a fourth electrode, operating in a second substantially planar physical zone that is substantially co-planar with the first planar physical zone, the third electrode and the fourth electrode each including at least one finger, the fingers of the third electrode and the fourth electrode each being separated from their nearest adjacent fingers by greater than 50 μm; and
a reagent located within the capillary passageway, the reagent combining with the bodily fluid to produce a redox reaction,
said reagent being located over at least one of the first and second sets of electrodes, and
the other of the first and second sets of electrodes either having said reagent located thereover or having no reagent located thereover.

22. The diagnostic strip of claim 21, wherein the first electrode pair is closer to the edge than the second electrode pair.

23. The diagnostic strip of claim 22, further comprising a fifth electrode situated farther from the edge than the first electrode pair and the second electrode pair.

24. The diagnostic strip of claim 23, wherein the fifth electrode is a single conductive lead.

25. The diagnostic strip of claim 24, wherein said fifth electrode has a width of at most 50 μm.

26. The diagnostic strip of claim 24, wherein said fifth electrode has a width of at least 50 μm.

27. The diagnostic strip of claim 23, wherein the fifth electrode is a plurality of conductive leads.

28. The diagnostic strip of claim 27, wherein the plurality of conductive leads each have a width of at most 50 μm and are not all electrically connected to each other on the strip.

29. The diagnostic strip of claim 21, wherein the second electrode pair is closer to the edge than the first electrode pair.

30. The diagnostic strip of claim 29, further comprising a fifth electrode situated farther from the edge than the first electrode pair and the second electrode pair.

31. The diagnostic strip of claim 30, wherein the fifth electrode is a single conductive lead.

32. The diagnostic strip of claim 31, wherein said fifth electrode has a width of at most 50 μm.

33. The diagnostic strip of claim 31, wherein said fifth electrode has a width of at least 50 μm.

34. The diagnostic strip of claim 30, wherein the fifth electrode is a plurality of conductive leads.

35. The diagnostic strip of claim 34, wherein the plurality of conductive leads extend parallel to the edge have a width of at most 50 μm and are not electrically connected to each other on the strip.

36. The diagnostic strip of claim 21, wherein the fingers of the first electrode and the second electrode are each separated from their nearest neighboring fingers of the first electrode pair by at most 30 μm at their nearest points.

37. The diagnostic strip of claim 21, wherein: the fingers of the first electrode and the second electrode are substantially rectangular in shape and at most 20 μm wide; and the fingers of the first electrode and the second electrode are each separated from their nearest neighbors of the first electrode pair by at most 20 μm at their nearest points.

38. The diagnostic strip of claim 21: further comprising a first electrical contact and a second electrical contact on the strip spaced apart from the first and second electrode pairs; wherein the first electrode and the third electrode are electrically connected to the first electrical contact, and the second electrode and the fourth electrode are electrically connected to the second electrical contact.

39. The diagnostic strip of claim 21: further comprising a first electrical contact, a second electrical contact, a third electrical contact, and a fourth electrical contact on the strip spaced apart from the first and second electrode pairs; wherein the first electrode is electrically connected to the first electrical contact, the second electrode is electrically connected to the second electrical contact, the third electrode is electrically connected to the third electrical contact, and the fourth electrode is electrically connected to the fourth electrical contact.

40. The test strip of claim 10, and further comprising a fourth electrode system in electrical communication with the passageway for determining when a sample has filled the passage to cover the first set of electrodes and the second set of electrodes.

41. The test strip of claim 40, wherein the fourth electrode system includes an electrode that is farther from the entrance of the passageway than both the first set of electrodes and the second set of electrodes.

42. The test strip of claim 40, wherein the fourth electrode system comprises a sample sufficiency working electrode and a sample sufficiency counter electrode, both of which are farther from the entrance of the passage than both the first set of electrodes and the second set of electrodes.

43. The test strip of claim 42, wherein the sample sufficiency working electrode and the sample sufficiency counter electrode each have a plurality of electrically connected fingers, each finger being substantially rectangular in shape and having a width between 5 μm and 50 μm.

44. The test strip of claim 1, wherein one of said first set of electrodes and said second set of electrodes comprises at least two electrodes having a width of less than 50 μm.

45. The test strip of claim 1, wherein one of said first set of electrodes and said second set of electrodes comprises at least two electrodes having a width greater than 50 μm.

46. The test strip of claim 1, wherein one of said first set of electrodes and said second set of electrodes comprises at least two electrodes having a width of less than 50 μm; and wherein the other of said first set of electrodes and said second set of electrodes comprises at least two electrodes having a width greater than 50 μm.

47. The test strip of claim 21, wherein no reagent material is over the first electrode pair.

48. A test strip for measuring the concentration of an analyte in a bodily fluid, the test strip defining a capillary passageway dimensioned so as to induce movement of a sample of bodily fluid along a predetermined path through the passageway extending inwardly from an entrance, the test strip comprising:

a first set of electrodes in electrical communication with the passageway, the first set of electrodes including a pair of electrodes with interdigitated fingers, wherein adjacent fingers are separated from one another by a gap;

a second set of electrodes in electrical communication with the passageway, the second set of electrodes including a pair of electrodes with interdigitated fingers, wherein adjacent fingers are separated from one another by a gap, with the gap between adjacent electrode fingers of the second electrode set being larger than the gap between adjacent electrode fingers of the first electrode set; and a reagent located within the capillary passageway, the reagent combining with the bodily fluid to produce a redox reaction, said reagent being located over at least one of the first and second sets of electrodes, and the other of the first and second sets of electrodes either having said reagent located thereover or having no reagent located thereover.

49. The test strip of claim 48, wherein the gap between adjacent electrode fingers of the first electrode set is 5 μm to 75 μm.

50. The test strip of claim 49, wherein the gap between adjacent electrode fingers of the first electrode set is 20 μm.

51. The test strip of claim 49, wherein the electrode fingers of the first electrode set are between 5 and 75 μm in width.

52. The test strip of claim 51, wherein the electrode fingers of the first electrode set are 20 μm in width.

53. The test strip of claim 48, wherein the electrode fingers of the second electrode set are between 5 and 75 μm in width.

54. The test strip of claim 53, wherein the electrode fingers of the second electrode set are 20 μm in width.

55. The test strip of claim 48, wherein the gap between adjacent electrode fingers of the second electrode set is 250 μm.

56. The test strip of claim 55, wherein the electrode fingers of the second electrode set are 250 μm in width.

57. The test strip of claim 55, wherein the gap between adjacent electrode fingers of the first electrode set is 5 μm to 75 μm.

58. The test strip of claim 48, wherein no reagent is over the other of the first and second electrode sets.

59. The test strip of claim 48, wherein said reagent is over both the first and the second sets of electrodes.

* * * * *